US009074211B2

(12) United States Patent
Woolf et al.

(10) Patent No.: US 9,074,211 B2
(45) Date of Patent: Jul. 7, 2015

(54) INHIBITION OF MAP4K4 THROUGH RNAI

(75) Inventors: Tod M. Woolf, Sudbury, MA (US); Joanne Kamens, Newton, MA (US); Anastasia Khvorova, Westborough, MA (US); William Salomon, Worcester, MA (US)

(73) Assignee: RXi Pharmaceuticals Corporation, Marlborough, MA (US)

( * ) Notice: Subject to any disclaimer, the term of this patent is extended or adjusted under 35 U.S.C. 154(b) by 199 days.

(21) Appl. No.: 13/130,194

(22) PCT Filed: Nov. 19, 2009

(86) PCT No.: PCT/US2009/006211
§ 371 (c)(1),
(2), (4) Date: Nov. 16, 2011

(87) PCT Pub. No.: WO2010/059226
PCT Pub. Date: May 27, 2010

(65) Prior Publication Data

US 2012/0059046 A1 Mar. 8, 2012

Related U.S. Application Data

(60) Provisional application No. 61/199,661, filed on Nov. 19, 2008.

(51) Int. Cl.
*C12N 15/113* (2010.01)

(52) U.S. Cl.
CPC ........ *C12N 15/1137* (2013.01); *C12N 2310/14* (2013.01); *C12N 2320/11* (2013.01); *C12Y 207/01037* (2013.01)

(58) Field of Classification Search
None
See application file for complete search history.

(56) References Cited

U.S. PATENT DOCUMENTS

| | | | |
|---|---|---|---|
| 4,201,860 | A | 5/1980 | Naito et al. |
| 4,235,871 | A | 11/1980 | Papahadjopoulos et al. |
| 4,415,732 | A | 11/1983 | Caruthers et al. |
| 4,426,330 | A | 1/1984 | Sears |
| 4,501,728 | A | 2/1985 | Geho et al. |
| 4,737,323 | A | 4/1988 | Martin et al. |
| 4,837,028 | A | 6/1989 | Allen |
| 4,897,355 | A | 1/1990 | Eppstein et al. |
| 4,904,582 | A | 2/1990 | Tullis |
| 4,958,013 | A | 9/1990 | Letsinger |
| 5,023,243 | A | 6/1991 | Tullis |
| 5,112,963 | A | 5/1992 | Pieles et al. |
| 5,416,203 | A | 5/1995 | Letsinger |
| 5,417,978 | A | 5/1995 | Tari et al. |
| 5,432,272 | A | 7/1995 | Benner |
| 5,459,255 | A | 10/1995 | Cook et al. |
| 5,466,786 | A | 11/1995 | Buhr et al. |
| 5,486,603 | A | 1/1996 | Buhr |
| 5,514,786 | A | 5/1996 | Cook et al. |
| 5,534,259 | A | 7/1996 | Zalipsky et al. |
| 5,556,948 | A | 9/1996 | Tagawa et al. |
| 5,578,718 | A | 11/1996 | Cook et al. |
| 5,580,731 | A | 12/1996 | Chang et al. |
| 5,580,972 | A | 12/1996 | Tu et al. |
| 5,587,469 | A | 12/1996 | Cook et al. |
| 5,591,721 | A | 1/1997 | Agrawal et al. |
| 5,591,722 | A | 1/1997 | Montgomery et al. |
| 5,591,843 | A | 1/1997 | Eaton |
| 5,594,121 | A | 1/1997 | Froehler et al. |
| 5,596,091 | A | 1/1997 | Switzer |
| 5,614,617 | A | 3/1997 | Cook et al. |
| 5,633,360 | A | 5/1997 | Bischofberger et al. |
| 5,643,889 | A | 7/1997 | Suhadolnik et al. |
| 5,646,126 | A | 7/1997 | Cheng et al. |
| 5,646,265 | A | 7/1997 | McGee |
| 5,658,731 | A | 8/1997 | Sproat et al. |
| 5,670,633 | A | 9/1997 | Cook et al. |
| 5,674,683 | A | 10/1997 | Kool |
| 5,681,940 | A | 10/1997 | Wang et al. |
| 5,681,941 | A | 10/1997 | Cook et al. |
| 5,684,143 | A | 11/1997 | Gryaznov et al. |
| 5,700,920 | A | 12/1997 | Altmann et al. |
| 5,736,392 | A | 4/1998 | Hawley-Nelson et al. |

(Continued)

FOREIGN PATENT DOCUMENTS

| | | | |
|---|---|---|---|
| AU | 2004206255 | B2 | 8/2004 |
| CN | 1 568 373 | A | 1/2005 |

(Continued)

OTHER PUBLICATIONS

Anderson et al., Experimental validation of the importance of seed complement frequency to SiRNA specificity. RNA. May 2008;14(5):853-61. doi: 10.1261/rna.704708. Epub Mar. 26, 2008.
Bartzatt, Cotransfection of nucleic acid segments by Sendai virus envelopes. Biotechnol Appl Biochem. Feb. 1989;11(1):133-5.
Bergan et al., Electroporation enhances c-myc antisense oligodeoxynucleotide efficacy. Nucleic Acids Res. Jul. 25, 1993;21(15):3567-73.
Bjergarde et al., Solid phase synthesis of oligodeoxyribonucleoside phosphorodithioates from thiophosphoramidites. Nucleic Acids Res. Nov. 11, 1991;19(21):5843-50.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.

(Continued)

*Primary Examiner* — Jennifer McDonald
(74) *Attorney, Agent, or Firm* — Wolf, Greenfield & Sacks, P.C.

(57) ABSTRACT

RNAi constructs directed to MAP4K4 that demonstrate unexpectedly high gene silencing activities, and uses thereof are disclosed. The blunt-ended constructs have a double-stranded region of 19-49 nucleotides. The constructs have selective minimal modifications to confer an optimal balance of biological activity, toxicity, stability, and target gene specificity. For example, the strands may be modified (e.g., one or both ends of the sense strand is modified by 2'-O-methyl groups), such that the construct is not cleaved by Dicer or other RNAse III, the antisense strand may also be modified by a 2'-O-methyl group at the penultimate 5'-end nucleotide to greatly reduce off-target silencing.

11 Claims, 3 Drawing Sheets

(56) References Cited

U.S. PATENT DOCUMENTS 5,767,099 A 6/1998 Harris et al.
5,777,153 A 7/1998 Lin et al.
5,780,053 A 7/1998 Ashley et al.
5,789,416 A 8/1998 Lum et al.
5,792,847 A 8/1998 Buhr et al.
5,830,430 A 11/1998 Unger et al.
5,830,653 A 11/1998 Froehler et al.
5,851,548 A 12/1998 Dattagupta et al.
5,855,910 A 1/1999 Ashley et al.
5,856,455 A 1/1999 Cook
5,914,396 A 6/1999 Cook et al.
5,948,767 A 9/1999 Scheule et al.
5,969,116 A 10/1999 Martin
5,976,567 A 11/1999 Wheeler et al.
5,981,501 A 11/1999 Wheeler et al.
6,001,841 A 12/1999 Cook et al.
6,005,096 A 12/1999 Matteucci et al.
6,020,483 A 2/2000 Beckvermit et al.
6,028,183 A 2/2000 Lin et al.
6,033,910 A 3/2000 Monia et al.
6,043,352 A 3/2000 Manoharan et al.
6,107,094 A 8/2000 Crooke
6,111,085 A 8/2000 Cook et al.
6,153,737 A 11/2000 Manoharan et al.
6,207,819 B1 3/2001 Manoharan et al.
6,271,358 B1 8/2001 Manoharan et al.
6,326,358 B1 12/2001 Manoharan
6,335,434 B1 1/2002 Guzaev et al.
6,346,416 B1 2/2002 Dean et al.
6,355,787 B1 3/2002 Beckvermit et al.
6,358,931 B1 3/2002 Cook et al.
6,395,492 B1 5/2002 Manoharan et al.
6,399,754 B1 6/2002 Cook
6,420,549 B1 7/2002 Cook et al.
6,432,963 B1 8/2002 Hisamichi et al.
6,444,806 B1 9/2002 Veerapanani et al.
6,476,205 B1 11/2002 Buhr et al.
6,506,559 B1 1/2003 Driver et al.
6,528,631 B1 3/2003 Cook et al.
6,531,584 B1 3/2003 Cook et al.
6,673,611 B2 1/2004 Thompson et al.
6,683,167 B2 1/2004 Metelev et al.
6,815,432 B2 11/2004 Wheeler et al.
6,849,726 B2 2/2005 Usman et al.
6,858,225 B2 2/2005 Semple et al.
7,041,824 B2 5/2006 Bordon-Pallier et al.
7,056,704 B2 6/2006 Tuschl et al.
7,078,196 B2 7/2006 Tuschl et al.
7,205,297 B2 4/2007 Beauchamp et al.
7,432,250 B2 10/2008 Crooke
7,538,095 B2 5/2009 Fire et al.
7,560,438 B2 7/2009 Fire et al.
7,595,387 B2 9/2009 Leake et al.
7,622,633 B2 11/2009 Fire et al.
7,629,321 B2 12/2009 Crooke
7,695,902 B2 4/2010 Crooke
7,745,608 B2 6/2010 Manoharan et al.
7,750,144 B2 7/2010 Zamore et al.
7,786,290 B2 8/2010 Woppmann et al.
7,829,693 B2 11/2010 Kreutzer et al.
8,110,674 B2 2/2012 Manoharan et al.
8,263,569 B2 9/2012 Baulcombe et al.
8,383,600 B2 2/2013 Czech et al.
8,664,189 B2 3/2014 Khvorova et al.
8,796,443 B2 8/2014 Khvorova et al.
8,815,818 B2 * 8/2014 Samarsky et al. ........... 514/44 A
2002/0132788 A1 9/2002 Lewis et al.
2002/0147332 A1 10/2002 Kaneko et al.
2002/0160393 A1 10/2002 Symonds et al.
2002/0162126 A1 10/2002 Beach et al.
2003/0004325 A1 1/2003 Cook et al.
2003/0077829 A1 4/2003 MacLachlan
2003/0108923 A1 6/2003 Tuschl et al.
2003/0139585 A1 7/2003 Uhlmann et al.
2003/0157030 A1 8/2003 Davis et al.
2003/0158403 A1 8/2003 Manoharan et al.
2003/0166282 A1 9/2003 Brown et al.
2004/0009938 A1 1/2004 Manoharan et al.
2004/0014956 A1 1/2004 Woolf et al.
2004/0014957 A1 1/2004 Eldrup et al.
2004/0018999 A1 1/2004 Beach et al.
2004/0054155 A1 3/2004 Woolf et al.
2004/0137471 A1 7/2004 Vickers et al.
2004/0167090 A1 8/2004 Monahan et al.
2004/0171033 A1 9/2004 Baker et al.
2004/0180351 A1 9/2004 Giese et al.
2004/0192629 A1 9/2004 Xu et al.
2004/0204377 A1 10/2004 Rana
2004/0229266 A1 11/2004 Tuschl et al.
2004/0241845 A1 12/2004 Desgroseillers et al.
2004/0248839 A1 12/2004 Kowalik
2004/0259247 A1 12/2004 Tuschl et al.
2005/0020521 A1 1/2005 Rana
2005/0032733 A1 2/2005 McSwiggen et al.
2005/0080246 A1 4/2005 Allerson et al.
2005/0107325 A1 5/2005 Manoharan et al.
2005/0142535 A1 6/2005 Damha et al.
2005/0181382 A1 8/2005 Zamore et al.
2005/0239731 A1 10/2005 McSwiggen et al.
2005/0255487 A1 11/2005 Khvorova et al.
2006/0009409 A1 1/2006 Woolf
2006/0035344 A1 2/2006 Pachuk et al.
2006/0127891 A1 6/2006 McSwiggen et al.
2006/0160133 A1 7/2006 Czech et al.
2006/0178324 A1 8/2006 Hadwiger et al.
2006/0178327 A1 8/2006 Yeung
2007/0031844 A1 * 2/2007 Khvorova et al. ................ 435/6
2007/0032441 A1 2/2007 McSwiggen et al.
2007/0166734 A1 7/2007 Bhat et al.
2007/0173476 A1 7/2007 Leake et al.
2007/0185047 A1 * 8/2007 Bhat et al. ....................... 514/44
2007/0231392 A1 10/2007 Wagner et al.
2007/0248659 A1 10/2007 Shanahan et al.
2007/0254850 A1 11/2007 Lieberman et al.
2007/0269889 A1 11/2007 Leake et al.
2008/0009012 A1 1/2008 Birmingham et al.
2008/0085869 A1 4/2008 Yamada et al.
2008/0311040 A1 12/2008 Berry et al.
2009/0131360 A1 * 5/2009 Woolf et al. .................... 514/44
2010/0069620 A1 3/2010 Zon
2010/0136695 A1 6/2010 Woolf
2011/0039914 A1 * 2/2011 Pavco et al. ................. 514/44 A
2011/0237522 A1 9/2011 Khvorova et al.
2011/0237648 A1 9/2011 Khvorova et al.
2011/0251258 A1 10/2011 Samarsky et al.
2011/0263680 A1 10/2011 Khvorova et al.
2012/0016005 A1 * 1/2012 Samarsky et al. ........... 514/44 A
2012/0040459 A1 2/2012 Khvorova et al.
2012/0065243 A1 3/2012 Woolf et al.
2013/0131141 A1 5/2013 Khvorova et al.
2013/0131142 A1 5/2013 Libertine et al.
2013/0197055 A1 8/2013 Kamens et al.
2014/0113950 A1 4/2014 Khvorova et al.
2014/0315974 A1 10/2014 Khvorova et al.
2014/0364482 A1 12/2014 Khvorova et al.

FOREIGN PATENT DOCUMENTS

EP 0 552 766 A2 7/1993
EP 1 214 945 A2 6/2002
EP 1 144 623 B9 3/2003
EP 1 352 061 B1 10/2003
EP 0 928 290 B9 3/2005
EP 1 407 044 B1 9/2007
EP 1 605 978 B1 1/2010
JP 4 095 895 B2 9/2004
WO WO 90/14074 A1 11/1990
WO WO 91/16024 A1 10/1991
WO WO 91/17424 A1 11/1991
WO WO 92/03464 A1 3/1992
WO WO 94/23028 A2 10/1994
WO WO 95/11910 A1 5/1995
WO WO 95/23162 A1 8/1995
WO WO 96/40964 A2 12/1996

(56) References Cited

FOREIGN PATENT DOCUMENTS

| | | | |
|---|---|---|---|
| WO | WO 03/012052 | A2 | 2/2003 |
| WO | WO 2004/001044 | A1 | 12/2003 |
| WO | WO 2004/065600 | A2 | 8/2004 |
| WO | WO 2004/065601 | A2 | 8/2004 |
| WO | WO 2004/090105 | A2 | 10/2004 |
| WO | WO 2005/019430 | A2 | 3/2005 |
| WO | WO 2005/079533 | A2 | 9/2005 |
| WO | WO 2005/097992 | A2 | 10/2005 |
| WO | WO 2006/019430 | A2 | 2/2006 |
| WO | WO 2006/039656 | A2 | 4/2006 |
| WO | WO 2006/065601 | A2 | 6/2006 |
| WO | WO 2006/128141 | A2 | 11/2006 |
| WO | WO 2007/030167 | A1 | 3/2007 |
| WO | WO 2007/089607 | A2 | 8/2007 |
| WO | WO 2008/036825 | A2 | 3/2008 |
| WO | WO 2008/109353 | A1 | 9/2008 |
| WO | WO 2009/044392 | A2 | 4/2009 |
| WO | WO 2010/011346 | A1 | 1/2010 |
| WO | WO 2010/027830 | A2 | 3/2010 |
| WO | WO 2010/033247 | A2 | 3/2010 |
| WO | WO 2010/042281 | A2 | 4/2010 |
| WO | WO 2011/109698 | A1 | 9/2011 |

OTHER PUBLICATIONS

Collins et al., A small interfering RNA screen for modulators of tumor cell motility identifies MAP4K4 as a promigratory kinase. Proc Natl Acad Sci U S A. Mar. 7, 2006; 103(10): 3775-3780.

Constantinides et al., Formulation and intestinal absorption enhancement evaluation of water-in-oil microemulsions incorporating medium-chain glycerides. Pharm Res. Oct. 1994;11(10):1385-90.

Ho et al., Preparation of microemulsions using polyglycerol fatty acid esters as surfactant for the delivery of protein drugs. J Pharm Sci. Feb. 1996;85(2):138-43.

Huang et al., Lipitoids—novel cationic lipids for cellular delivery of plasmid DNA in vitro. Chem Biol. Jun. 1998;5(6):345-54.

Kamata et al., Amphiphilic peptides enhance the efficiency of liposome-mediated DNA transfection. Nucleic Acids Res. Feb. 11, 1994;22(3):536-7.

Lemaitre et al., Specific antiviral activity of a poly(L-lysine)-conjugated oligodeoxyribonucleotide sequence complementary to vesicular stomatitis virus N protein mRNA initiation site. Proc Natl Acad Sci U S A. Feb. 1987;84(3):648-52.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Murphy et al., A combinatorial approach to the discovery of efficient cationic peptoid reagents for gene delivery. Proc Natl Acad Sci U S A. Feb. 17, 1998;95(4):1517-22.

Reichhart et al., Splice-activated UAS hairpin vector gives complete RNAi knockout of single or double target transcripts in *Drosophila melanogaster*. Genesis. Sep.-Oct. 2002;34(1-2):160-4.

Schell, Uptake of polynucleotides by mammalian cells. XIV. Stimulation of the uptake of polynucleotides by poly(L-lysine). Biochim Biophys Acta. Mar. 27, 1974;340(3):323-33.

Shi, Mammalian RNAi for the masses. Trends Genet. Jan. 2003;19(1):9-12.

Su et al., NIK is a new Ste20-related kinase that binds NCK and MEKK1 and activates the SAPK/JNK cascade via a conserved regulatory domain. EMBO J. Mar. 17, 1997;16(6):1279-90.

Sui et al., A DNA vector-based RNAi technology to suppress gene expression in mammalian cells. Proc Natl Acad Sci U S A. Apr. 16, 2002;99(8):5515-20.

Tang et al., An RNA interference-based screen identifies MAP4K4/NIK as a negative regulator of PPARgamma, adipogenesis, and insulin-responsive hexose transport. Proc Natl Acad Sci U S A. Feb. 14, 2006;103(7):2087-92. Epub Feb. 3, 2006.

Uhlmann et al., Antisense oligonucleotides: a new therapeutic principle. Chem Rev. 1990;90(4):543-84.

Vlassov et al., Transport of oligonucleotides across natural and model membranes. Biochim Biophys Acta. Jun. 29, 1994;1197(2):95-108.

Wagner et al., Transferrin-polycation-DNA complexes: the effect of polycations on the structure of the complex and DNA delivery to cells. Proc Natl Acad Sci U S A. May 15, 1991;88(10):4255-9.

Xue et al., Mesodermal patterning defect in mice lacking the Ste20 NCK interacting kinase (NIK). Development. May 2001;128(9):1559-72.

Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.

Zuckermann et al., Design, construction and application of a fully automated equimolar peptide mixture synthesizer. Int J Pept Protein Res. Dec. 1992;40(6):497-506.

Zuckermann et al., Efficient method for the preparation of peptoids [oligo(N-substituted glycines)] by submonomer solid-phase synthesis. Journal of the American Chemical Society. 1992;114 (26):10646-10647.

[No Author Listed] RedChip Small-Cap Investor Conference. RXI Pharmaceuticals (Nasdaq RXII). Jun. 16, 2009 Presentation. 5 pages.

Alahari et al , Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.

Aleckovic et al., RNAi at Oxford. J RNAi Gene Silencing. May 27, 2008;4(1):266-8.

Aouadi et al., Orally delivered siRNA targeting macrophage Map4k4 suppresses systemic inflammation. Nature. Apr. 30, 2009;458(7242):1180-4. doi: 10.1038/nature07774.

Baigude et al., Design and creation of new nanomaterials for therapeutic RNAi. ACS Chem Biol. Apr. 24, 2007;2(4):237-41.

Braasch et al., RNA Interference in Mammalian Cells by Chemically-Modified RNA. Biochem. 2003;42(26):7967-75.

Brown et al., Light at the end of the tunnel. J RNAi Gene Silencing. Jul. 28, 2006;2(2):175-7.

Chiu et al., siRNA function in RNAi: a chemical modification analysis. RNA. Sep. 2003;9(9):1034-48.

Choung et al. Chemical modification of siRNAs to improve serum stability without loss of efficacy. Biochem Biophys Res Commun. Apr. 14, 2006;342(3):919-27.

Czauderna et al., Structural variations and stabilising modifications of synthetic siRNAs in mammalian cells. Nucleic Acids Res. Jun. 1, 2003;31(11):2705-16.

De Smidt et al., Association of antisense oligonucleotides with lipoproteins prolongs the plasma half-life and modifies the tissue distribution. Nucleic Acids Res. Sep. 11, 1991;19(17):4695-700.

Debart et al., Chemical modifications to improve the cellular uptake of oligonucleotides. Curr Top Med Chem. 2007;7(7):727-37.

Dykxhoorn et al., The silent treatment: siRNAs as small molecule drugs. Gene Ther. Mar. 2006;13(6):541-52.

Elbashir et al., Functional anatomy of siRNAs for mediating efficient RNAi in *Drosophila melanogaster* embryo lysate. EMBO J. Dec. 3, 2001;20(23):6877-88.

Fedorov et al., Off-target effects by siRNA can induce toxic phenotype. RNA. Jul. 2006;12(7):1188-96. Epub May 8, 2006.

Ferentz et al., Disulfide-crosslinked oligonucleotides. Journal of the American Chemical Society. 1991;113 (10): 4000-4002.

Genbank Submission; NCBI, Accession No. NM_004834; Bouzakri et al., Oct. 24, 2008. 8 Pages.

Jackson et al., Position-specific chemical modification of siRNAs reduces “off-target” transcript silencing. RNA. Jul. 2006;12(7):1197-1205. Epub May 8, 2006.

Kim et al., Synthetic dsRNA Dicer substrates enhance RNAi potency and efficacy. Nat Biotechnol. Feb. 2005;23(2):222-6. Epub Dec. 26, 2004.

Kim et al., Systemic and specific delivery of small interfering RNAs to the liver mediated by apolipoprotein A-I. Mol Ther. Jun. 2007;15(6):1145-52. Epub Apr. 17, 2007.

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.

Kubo et al., Modified 27-nt dsRNAs with dramatically enhanced stability in serum and long-term RNAi activity. Oligonucleotides. 2007 Winter;17(4):445-64.

(56) References Cited

OTHER PUBLICATIONS

Layzer et al., In vivo activity of nuclease-resistant siRNAs. RNA. May 2004;10(5):766-71.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Rep. Mar. 2006;7(3):314-20. Epub Jan. 20, 2006.
Li et al., Surface-modified LPD nanoparticles for tumor targeting. Ann N Y Acad Sci. Oct. 2006;1082:1-8.
Macrae et al., Structure of Dicer and mechanistic implications for RNAi. Cold Spring Harb Symp Quant Biol. 2006;71:73-80.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Murchison et al., Characterization of Dicer-deficient murine embryonic stem cells. Proc Natl Acad Sci U S A. Aug. 23, 2005;102(34):12135-40. Epub Aug. 12, 2005.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Parrish et al., Functional anatomy of a dsRNA trigger: differential requirement for the two trigger strands in RNA interference. Mol Cell. Nov. 2000;6(5):1077-87.
Rajeev et al., 2'-modified-2-thiothymidine oligonucleotides. Org Lett. Aug. 21, 2003;5(17):3005-8.
Rump et al., Preparation of conjugates of oligodeoxynucleotides and lipid structures and their interaction with low-density lipoprotein. Bioconjug Chem. May-Jun. 1998;9(3):341-9.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Soutschek et al., Therapeutic silencing of an endogenous gene by systemic administration of modified siRNAs. Nature. Nov. 11, 2004;432(7014):173-8.
Wolfrum et al., Mechanisms and optimization of in vivo delivery of lipophilic siRNAs. Nat Biotechnol. Oct. 2007;25(10):1149-57. Epub Sep. 16, 2007.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

* cited by examiner

SEQUENCE LISTING

<160> NUMBER OF SEQ ID NOS: 57

<210> SEQ ID NO 1
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 1
gccagaaugu guugcugacu gagaa 25

<210> SEQ ID NO 2
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 2
uucucaguca gcaacacauu cuggc 25

<210> SEQ ID NO 3
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 3
ugagaaugca gaggugaaac uuguu 25

<210> SEQ ID NO 4
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 4
aacaaguuuc accucugcau ucuca 25

<210> SEQ ID NO 5
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 5
cauccaauga gagcacuguu ucuca 25

<210> SEQ ID NO 6
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 6
ugagaaacag ugcucucauu ggaug 25

<210> SEQ ID NO 7
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 7
gaucagccaa augaaaggca aguua 25

<210> SEQ ID NO 8
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 8
uaacuugccu uucauuuggc ugauc 25

<210> SEQ ID NO 9
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 9
ucagccaaau gaaaggcaag uuaga 25

<210> SEQ ID NO 10
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 10
ucuaacuugc cuuucauuug gcuga 25

<210> SEQ ID NO 11
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 11
cuuugaagag uucuguggaa gucua 25

<210> SEQ ID NO 12
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 12
uuugaagagu ucuguggaag ucuau 25

<210> SEQ ID NO 13
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 13
gaaaggcaag uuagaaucca gcuua 25

<210> SEQ ID NO 14
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 14
uaagcuggau ucuaacuugc cuuuc 25

<210> SEQ ID NO 15
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 15
aggcgacggc uagaagagca acaaa 25

<210> SEQ ID NO 16
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 16
uuuguugcuc uucuagccgu cgccu 25

<210> SEQ ID NO 17
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 17
agauguacgg ccaccucaca aagua 25

<210> SEQ ID NO 18
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 18
uacuuuguga gguggccgua caucu 25

<210> SEQ ID NO 19

<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 19
aguccgcuag uagcacacuc cagaa 25

<210> SEQ ID NO 20
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 20
uucuggagug ugcuacuagc ggacu 25

<210> SEQ ID NO 21
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 21
ccgcuaguag cacacuccag aaaca 25

<210> SEQ ID NO 22
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 22
uguuucugga gugugcuacu agcgg 25

<210> SEQ ID NO 23
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 23
gcuaguagca cacuccagaa acaca 25

<210> SEQ ID NO 24
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 24
uguguuucug gagugugcua cuagc 25

<210> SEQ ID NO 25
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 25
agcacacucc agaaacacaa aucuu 25

<210> SEQ ID NO 26
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 26
aagauuugug uuucuggagu gugcu 25

<210> SEQ ID NO 27
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 27
acaagaagag guuuaacucu gagau 25

<210> SEQ ID NO 28
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 28
aucucagagu uaaaccucuu cuugu 25

<210> SEQ ID NO 29
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 29
agaagagguu uaacucugag auucu 25

<210> SEQ ID NO 30
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 30
agaaucucag aguuaaaccu cuucu 25

<210> SEQ ID NO 31
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 31
aaggucuauc cucuuaucaa ccgaa 25

<210> SEQ ID NO 32
<211> LENGTH: 25
<212> TYPE: RNA

<213> ORGANISM: Artificial Sequence
<220> FEATURE:
<223> OTHER INFORMATION: Synthetic Oligonucleotide

<400> SEQUENCE: 32
uucgguugau aagaggauag accuu 25

<210> SEQ ID NO 33
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 33
ucuuaucaac cgaagacgau uucaa 25

<210> SEQ ID NO 34
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 34
uugaaaucgu cuucgguuga uaaga 25

<210> SEQ ID NO 35
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 35
ugucuuggug acaauaucug gcaaa 25

<210> SEQ ID NO 36
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 36
uuugccagau auugucacca agaca 25

<210> SEQ ID NO 37
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 37
uacgugucua cuauuugucc ugguu 25

<210> SEQ ID NO 38
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 38
aaccaggaca aauaguagac acgua 25

<210> SEQ ID NO 39
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 39
cgugucuacu auuuguccug guuaa 25

<210> SEQ ID NO 40
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 40
uuaaccagga caaauaguag acacg 25

<210> SEQ ID NO 41
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 41
gauugcuuug aagaguucug uggaa 25

<210> SEQ ID NO 42
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 42
uuccacagaa cucuucaaag caauc 25

<210> SEQ ID NO 43
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 43
acugguggau cucacuguug aggaa 25

<210> SEQ ID NO 44
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 44
uuccucaaca gugagaucca ccagu 25

<210> SEQ ID NO 45
<211> LENGTH: 25
<212> TYPE: RNA
<213> ORGANISM: Artificial Sequence
<220> FEATURE:

<223> OTHER INFORMATION: Synthetic Oligonucleotide

<400> SEQUENCE: 45
ugauguggau ucaggaucag ucuau 25

<210> SEQ ID NO 46
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 46
auagacugau ccugaaucca cauca 25

<210> SEQ ID NO 47
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 47
gauucaggau cagucuauga cauuu 25

<210> SEQ ID NO 48
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 48
aaaugucaua gacugauccu gaauc 25

<210> SEQ ID NO 49
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 49
acugguggau cucacugugg aggaa 25

<210> SEQ ID NO 50
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 50
cauuacuggu ggaucucacu guuga 25

<210> SEQ ID NO 51
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 51
cauuacuggu ggaucucacu gugga 25

<210> SEQ ID NO 52
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 52
uagacuucca cagaacucuu caaag 25

<210> SEQ ID NO 53
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 53
guccgcuagu agcacacucc agaaa 25

<210> SEQ ID NO 54
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 54
caguccgcua guagcacacu ccaga 25

<210> SEQ ID NO 55
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 55
aauugcuuug aagaguucug uggaa 25

<210> SEQ ID NO 56
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 56
ugauugcuuu gaagaguucu gugga 25

<210> SEQ ID NO 57
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 57
uaauugcuuu gaagaguucu gugga 25

INHIBITION OF MAP4K4 THROUGH RNAI

RELATED APPLICATIONS

This application is a national stage filing under 35 U.S.C. §371 of international application PCT/US2009/006211, filed Nov. 19, 2009, which was published under PCT Article 21(2) in English and claims the benefit under 35 U.S.C. §119(e) to U.S. Provisional Application Ser. No. 61/199,661, entitled "Inhibition of MAP4K4 through RNAi," filed on Nov. 19, 2008, the disclosures of which are herein incorporated by reference in their entireties.

BACKGROUND OF THE INVENTION

MAP4K4 is a mammalian serine/threonine protein kinase that belongs to a group of protein kinases related to *Saccharomyces cerevisiae* Sterile 20 (STE20). MAP4K4 (also known as NIK for Nck interacting kinase) was first identified in a mouse screen for proteins that interact with the SH3 domain of Nck (Su et al. (1997). Since its discovery, MAP4K4 has been and continues to be linked to wide range of physiological functions.

MAP4K4 is proposed to link protein tyrosine kinase signals to JNK activation and may play a role in cytoskeletal regulation (Xue et al., *Development* (2000), 128, 1559-1572). MAP4K4 has been found to be essential for development in mammalian cells. $Nik^{-/-}$ mouse embryos have been show to die postgastrulation. Patterning experiments in mice have suggested that NIK plays a critical and specific role in regulating the migration of cells that arise from the region of the primitive streak just posterior to the node (Xue et al., *Development* (2000), 128, 1559-1572). These experiments also led to the suggestion that MAP4K4 may regulate the mesodermal migration that contributes to the elongation of the body axis. Xue et al. have further speculated that a NCK/MAP4K4 complex may be required for segmentation of presomitic mesoderm into somites.

More recently, MAP4K4 has also been shown to be involved in metabolic disorders. For example, silencing of MAP4K4 resulted in an increase in the expression of a nuclear hormone receptor, PPARγ, that regulates the expression of genes responsible for adipocyte differentiation (Tang et al., *Proc. Natl. Acad. Sci.* (2006), 103, 2087-2092). Such genes include, for example, the insulin-responsive facilitative glucose transporter isoform 4 (GLUT4), which mediates insulin-dependent glucose transport into both muscle and adipose tissue. Indeed, several studies have revealed that a MAP4K4-dependent signaling pathway potently inhibits PPARγ-responsive gene expression, adipogenesis, and insulin-stimulated glucose transport.

SUMMARY OF THE INVENTION

The present invention is directed in some aspects to RNAi constructs comprising MAP4K4-specific sequences and methods pertaining to their use in MAP4K4 silencing. Accordingly, the present invention provides compositions and methods for increasing the efficiency of inhibiting MAP4K4 expression through RNA interference.

In one aspect, the present invention relates to an RNAi construct for inhibiting expression of a MAP4K4 gene, comprising a guide sequence that hybridizes to a target sequence on an mRNA of the MAP4K4 gene and inhibits the expression of the MAP4K4 gene through an RNA interference mechanism, wherein said target sequence is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

In one particular embodiment, the RNAi construct comprises a single-stranded polynucleotide that forms a hairpin structure which includes a double-stranded stem and a single-stranded loop, wherein the double-stranded stem can be cleaved by Dicer to produce an siRNA having a guide sequence that hybridizes to a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

In another embodiment, the RNAi construct comprises an siRNA having a guide sequence that hybridizes to a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

In another embodiment, the RNAi construct comprises an siRNA having a guide sequence that is any one of SEQ ID NO. 2, 4, 6, 8, 10, 14, 16, 18, 20, 22, 24, 26, 28, 30, 32, 34, 36, 38, 40, 42, 44, 46, 48, or 52.

In certain embodiments of the invention, the RNAi construct comprises a single-stranded polynucleotide that forms a hairpin structure. The hairpin structure includes a double-stranded stem and a single-stranded loop, wherein the double-stranded stem has a 5'-stem sequence having a 5'-end, and a 3'-stem sequence having a 3'-end. The 5'-stem sequence and at least a portion of said loop form the guide sequence that hybridizes to a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

In a related embodiment, the 5'-stem sequence, the loop, and at least a portion of the 3'-stem sequence collectively form the guide sequence that hybridizes to a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

In certain embodiments, the single-stranded polynucleotide is an RNA.

In certain embodiments, at least 12 nucleotides from the 5'-end of the single-stranded polynucleotide are 100% complementary to the target sequence.

In certain embodiments, at least one nucleotide is modified to improve resistance to nucleases, serum stability, target specificity, tissue distribution, and/or cell-permeability of the polynucleotide.

In certain embodiments, the modified nucleotides are modified on the sugar moiety, the base, and/or the phosphodiester linkage.

In certain embodiments, the modification is at position 2 from the 5'-end of the polynucleotide.

In certain embodiments, the modification is a 2'-O-alkyl or 2'-halo group.

In certain embodiments, the modification comprises 2'-O-methyl modification at alternative nucleotides, starting from either the first or the second nucleotide from the 5'-end.

In certain embodiments, the modification comprises 2'-O-methyl modification of one or more randomly selected pyrimidine nucleotides (C or U).

In certain embodiments, the modification comprises 2'-O-methyl modification of one or more nucleotides within the loop. For example, the modification is either limited to one or more nucleotides within the loop, or additionally including 1, 2, 3, 4, 5, or 6 more nucleotide(s) of the guide sequence within the double-stranded stem region just 5' to said loop.

In certain embodiments, the modification comprises 2'-O-methyl modification, wherein no more than 4 consecutive nucleotides are modified.

In certain embodiments, all nucleotides in the 3'-end stem region are modified.

In certain embodiments, all nucleotides in the sense sequence are modified.

In certain embodiments, the modification is a phosphate analog.

In certain embodiments, the modification is a phosphorothioate linkage.

In a related embodiment, the phosphorothioate linkage is limited to one or more nucleotides within said loop. In another aspect, the phosphorothioate linkage is limited to one or more nucleotides within said loop, and 1, 2, 3, 4, 5, or 6 more nucleotide(s) of the guide sequence within the double-stranded stem region just 5' to said loop.

In certain embodiments, the modification comprises hydrophobic modification to one or more bases. For example, said one or more bases are C or G. In one aspect, the hydrophobic modification comprises an isobutyl group.

In one embodiment, the guide sequence is about 15-21 nucleotides in length, or about 19-21 nucleotides in length.

In certain embodiments, the polynucleotide is 15-29 nucleotides in length, or about 25-26 nucleotides in length.

In another embodiment, the hairpin structure is not a substrate for Dicer.

In certain embodiments, the double-stranded stem of the hairpin structure is less than 21 base pairs in length. In another aspect, the double-stranded stem is less than about 20 base pairs in length, or is about 5-15 base pairs in length, or about 10 base pairs in length. In certain embodiments, the double-stranded stem is at least 11 base pairs in length, preferably at least 12 base pairs in length.

In other embodiments, the single-stranded loop is 4, 5, 6, 7, 8, 9, 10, 11, 12, 13, or 14 nucleotides in length.

In certain embodiments, the single-stranded polynucleotide comprises an overhang on the 3'-end and/or an overhang on the 5'-end.

In certain embodiments, the 3'-stem sequence is 100% complementary to the 5'-stem sequence. In other embodiments, the 3'-stem sequence is less than 100% complementary to the 5'-stem sequence.

In certain embodiments, the 3'-stem sequence of the double-stranded stem comprises one or more universal base-pairing nucleotides.

In yet another embodiments, the RNAi constructs of the present invention comprise a double-stranded (dsRNA) construct of 25 base pairs in length, wherein the dsRNA comprises (1) a sense strand having a 5'-end and a 3'-end wherein said sense strand corresponds to a target sequence of an mRNA of the MAP4K4 gene, and (2) a guide sequence having a 5'-end and a 3'-end that hybridizes to the sense strand or to the target sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57 under physiological condition of a cell or under high stringency hybridization condition.

In certain embodiments, the dsRNA is blunt-ended.

In certain embodiments, the sense strand comprises one or more consecutive 2'-modified ribose sugar at east of said 5'- and 3'-ends of said sense strand. For example, in one aspect, the sense strand comprises 12 and 10 consecutive 2'-modified ribose sugars at the 5'-end and the 3'-end nucleotides, respectively. In another aspect, the sense strand comprises 4 consecutive 2'-modified ribose sugars at both ends.

In certain embodiments, the 2'-modified ribose sugars are 2'-O-alkyl nucleotides, 2'-deoxy-2'-fluoro nucleotides, 2'-deoxy nucleotides, 2'-H (deoxyribonucleotides), or combination thereof.

In certain embodiments, the guide sequence of the dsRNA further comprises a 2'-modified ribose sugar. For example, the 2'-ribose sugar is 2'-O-alkyl nucleotides, 2'-deoxy-2'-fluoro nucleotides, 2'-deoxy nucleotides, 2'-H (deoxyribonucleotides), or combination thereof.

In certain embodiments, the guide sequence of the dsRNA comprises a 2'-modification at the 2" nucleotide from the 5'-end of the guide sequence.

In certain embodiments, the guide sequence comprises four consecutive 2'-modification at the 3'-most end.

In certain embodiments, the MAP4K4 gene is present in a cell. In a related embodiment, the MAP4K4 gene is an endogenous gene.

In certain embodiments, the cell is of eukaryotic origin. For example, the cell is from a mammal, nematode, or insect.

In certain embodiments, the MAP4K4 gene is human or mouse.

In certain embodiments, the target sequence of the present invention is at least 95% identical between the mouse and human sequences.

In certain embodiments, the constructs of the present invention reduce the MAP4K4 mRNA level by at least 60% of normal level.

In certain embodiments, the constructs of the present invention exhibit low off-target effects. For example, the construct exhibits a seed region frequency of less than 6000, preferably less than 350.

In certain embodiments, the construct of the present invention associates with RISC.

In another aspect, the invention provides a vector expressing the RNAi constructs of the present invention. In another aspect, the invention provides a cell comprising the vector expressing the RNAi constructs of the present invention. In another aspect, the invention provides a cell comprising any of the RNAi constructs of the present invention.

In certain embodiments, the cell is a mammalian cell in culture. For example, the cell is a human cell.

The present invention also provides a composition comprising any of the RNAi construct described herein and a pharmaceutically acceptable carrier or diluent.

Also provided is a method for inhibiting the expression of a MAP4K4 gene in a mammalian cell, comprising contacting the mammalian cell with an RNAi construct according to the invention, or a vector that expresses an RNAi construct as described herein.

In a related embodiment, the mammalian cell is in culture. For example, the mammalian cell is a human cell.

In certain embodiments, the mammalian cell is contacted in the presence of a delivery agent. For example, the delivery reagent comprises a lipid. In one aspect, the lipid is a cationic lipid. In another embodiment, the delivery reagent is a liposome. In other aspects, the delivery reagent comprises beta-glucan, chitosan, and/or PEI.

In another aspect an RNAi construct for inhibiting expression of a MAP4K4 gene, comprising a guide sequence that hybridizes to a target sequence on an mRNA of the MAP4K4 gene and inhibits the expression of the MAP4K4 gene through an RNA interference mechanism, wherein the RNAi construct is a duplex selected from the group consisting of Duplex numbers 1-25 from Table 1 and 3 is provided.

In one aspect, the invention provides a method of treating a patient for a disease characterized by overexpression of a MAP4K4 gene, comprising administering to the patient an RNAi construct according to the present invention, wherein the RNAi construct mediates guide sequence-dependent reduction in MAP4K4 expression.

In another aspect, the invention also provides a method of inhibiting expression of a MAP4K4 gene with an RNAi construct according to the present invention, wherein the RNAi construct mediates guide sequence-dependent reduction in MAP4K4 expression.

In another aspect the invention is a composition comprising an oligonucleotide that is any one of SEQ ID NO. 2, 4, 6, 8, 10, 14, 16, 18, 20, 22, 24, 26, 28, 30, 32, 34, 36, 38, 40, 42, 44, 46, 48, or 52.

In another aspect the invention is a composition comprising an oligonucleotide that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 or 57.

It is contemplated that any embodiment of the invention described herein can be combined with any one or more other embodiments whenever applicable, even though the different embodiments are separately described in different sections or aspects of the invention.

DETAILED DESCRIPTION OF THE INVENTION

I. Overview

Figure 1:
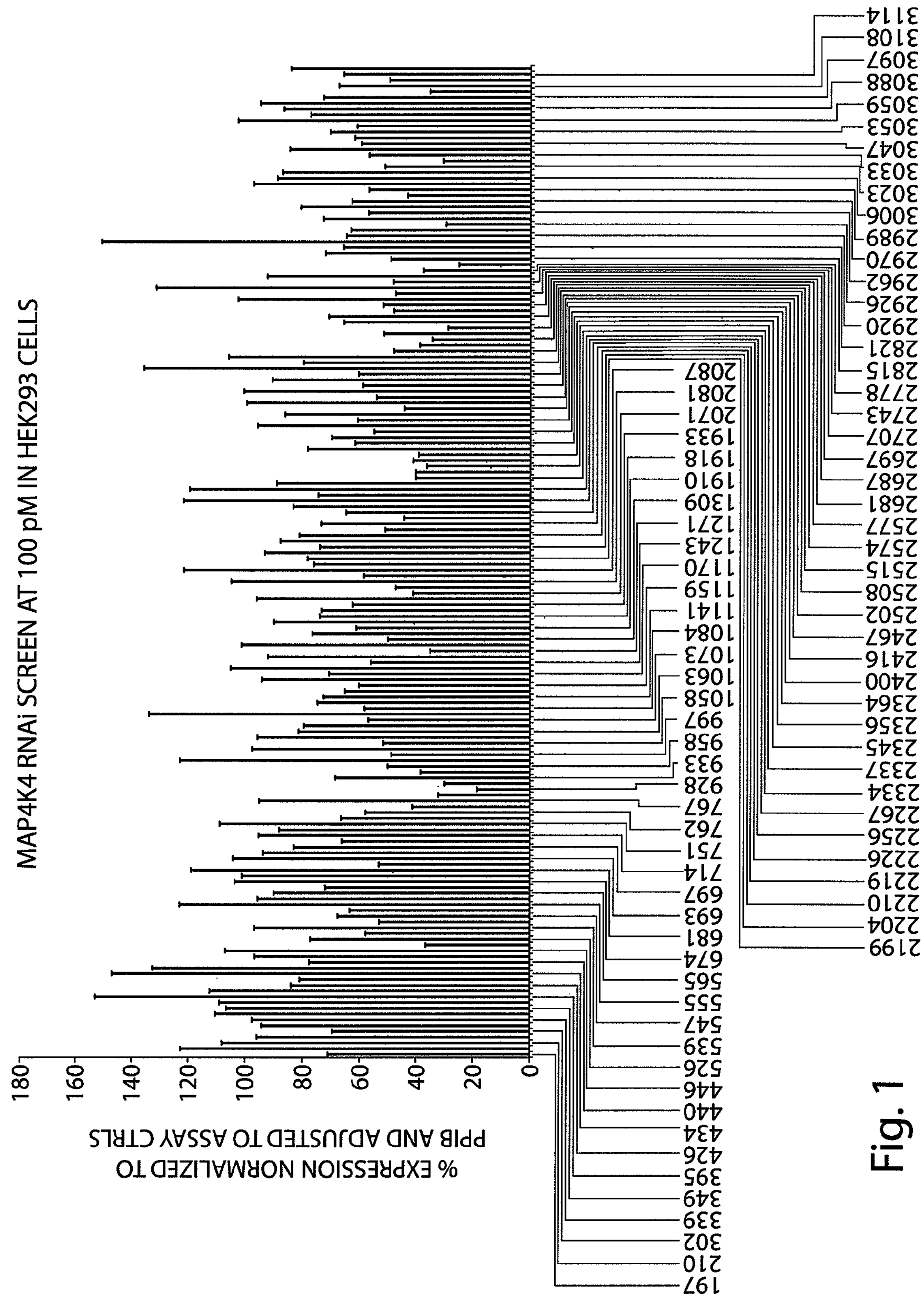
FIG. 1 shows an RNA screen across the entire length of the human MAP4K4 gene (NM_004834.3). HEK293 cells were transfected at 0.1 nM active RNA concentration and target mRNA was measured 24 hours post-transfection. Three duplexes: 10, 20 and 21 corresponding to start sites 2337, 2926, and 3028, respectively, of MAP4K4 were chosen based on their activity and homology to the mouse MAP4K4 gene (NM_008696.2).

The present invention is related, in part, to compositions and therapeutic methods for the regulation of MAP4K4 activity. To this end, the invention is directed to methods of identifying agents and the use of identified agents for regulating MAP4K4 in dysregulation, or in conditions that may benefit from silencing of MAP4K4 to below physiological levels. In particular, described herein is MAP4K4 silencing through the use of certain MAP4K4 sequence-specific RNAi constructs which exhibit unexpectedly high gene silencing activity. The present invention also includes methods for identifying sequences within a MAP4K4 gene that can be used to design effective RNAi constructs. RNAi constructs of the present method are designed and manipulated according to the methods described herein to yield highly stable and potent constructs with low levels of off-targeting effects.

In general, the invention is directed to RNAi constructs for inhibiting the expression of MAP4K4, wherein said RNAi construct comprises a guide sequence that hybridizes to a target sequence on an mRNA of the MAP4K4 gene and inhibits the expression of the MAP4K4 gene through an RNAi interference mechanism, and wherein the target sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57. Described below are a few exemplary constructs that can be used in the context of the subject sequences and be used in the methods of the invention described herein. It is understood, however, that any given types of RNAi construct known in the art may be applicable. For example, in addition to the specific embodiments described herein (e.g., the double-stranded duplex and the "mimRNA" structures), the present invention relates to an RNAi construct that comprises a single-stranded polynucleotide that forms a hairpin structure, which includes a double-stranded stem and a single-stranded loop, wherein the double-stranded stem can be cleaved by Dicer to produce an siRNA having a guide sequence that hybridizes to a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57. Further still, the present invention includes an siRNA (such as a duplex of 19 nucleotides, with or without 3'-overhangs), as described in the art, comprising a guide sequence that hybridizes to a to sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57 under physiological condition of a cell or under high stringency hybridization condition.

Double-Stranded Duplex Structures

In one aspect, the invention provides a double-stranded RNA (dsRNA) construct, preferably of 25 base pairs in length, for inhibiting expression of a MAP4K4 gene. Such dsRNA construct comprises a sense strand having a 5'-end and a 3'-end that corresponds to a region within an mRNA transcript of the MAP4K4 gene, and an antisense strand having a 5'-end and a 3'-end that hybridizes to the sense strand under physiological conditions of a cell or under high stringency hybridization conditions. In certain embodiments, the sense strand comprises a sequence that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57. The dsRNA construct of the present invention inhibits expression of MAP4K4 in a sequence-dependent manner.

In certain embodiments, the sense strand comprises one or more consecutive 2'-modified ribose sugar at each of said 5'- and 3'-ends of said sense strand. In certain preferred embodiments, the sense strand comprises 12 and 10 consecutive 2'-modified ribose sugar at each of said 5'-end and 3'-end nucleotides, respectively. In certain embodiments, each end of the sense strand comprises a continuous stretch of 2'-modified ribose sugars, although each end may have the same number or different numbers of 2'-modified ribose sugars. In other aspects, the sense strand comprises 4 consecutive 2'-modified ribose sugars at both ends.

For a 25-mer construct, each end of the sense strand may comprise, independently, 4-16 2'-modified nucleotides and/or non-hydrolyzable linkages (e.g., phosphothioate linkages). The number of the modified bases may be adjusted depending on the overall length of the construct. For example, for a 27-mer, each end of the sense strand may comprise, independently, 4-18 2'-modified nucleotides and/or phosphothioate linkages, etc.

In other embodiments, the antisense strand comprises an antisense sequence that is any one of SEQ ID NO. 2, 4, 6, 8, 10, 14, 16, 18, 20, 22, 24, 26, 28, 30, 32, 34, 36, 38, 40, 42, 44, 46, 48, or 52

In certain embodiments, the antisense strand is unmodified. In other aspects of the invention, the antisense (guide) strand further comprises a 2'-modified ribose sugar. Such 2'-modification of the antisense strand is at the $2^{nd}$ nucleotide from the 5' end of the antisense strand. In another embodiment, the antisense strand comprises four consecutive 2'-modification at the 3'-most end of the antisense strand.

As used herein, "2'-modified ribose sugar" includes those ribose sugars that do not have a 2'-OH group. For example, the 2'-modified ribose sugar may be 2'-O-alkyl nucleotides, 2'-deoxy-2'-fluoro nucleotides, 2'-deoxy nucleotides, 2'-H (deoxyribonucleotides), or combination thereof. In certain embodiments, the 2'-modified nucleotides are pyrimidine nucleotides (e.g., C/U). The 2'-O-alkyl nucleotides may be, for example, 2'-O-methyl nucleotides, or 2'-O-allyl nucleotides.

In another embodiment, dsRNA constructs of the present invention comprise MAP4K4 sequences of human or mouse origin. Additionally, in certain preferred embodiments, the sense strands of the dsRNA correspond to regions of the MAP4K4 mRNA sequence that is at least about 80%, 85%, 90%, 95%, 97%, or 99% identical between the mouse and human sequences.

In other aspects of the invention, the dsRNA construct significantly (e.g., at least about 40%, 45%, 50%, 55%, 60%, 65%, 70%, 75%, 80%, 85%, 90%, 95% or more) reduces a MAP4K4 mRNA level relative to normal (physiological) or physiologically aberrant (e.g., overexpression) levels. In preferred aspects of the invention, the dsRNA construct reduces a MAP4K4 mRNA level by at least 60% of a normal level.

In certain embodiments, the dsRNA of the invention with the above-referenced modifications exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified antisense modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

In certain embodiments, a suitable dsRNA MAP4K4 sequence to be used as an siRNA construct in the present invention adheres to what has been described as having a low or moderate seed complement frequency (SCF). See, for example, Anderson et al. (*RNA,* 2008, 14: 853-861). SCF refers to the pairing between the hexamer seed region of an siRNA antisense strand (nucleotides 2-7) and complementary sequences in the 3' UTR of mature transcripts. This association has been implicated as a contributing factor in off-targeting effects. As defined herein, siRNA sequences with low (<350) or moderate (~350-6000) incidents of complementation with the 3' UTR (i.e., low or moderate SCF) exhibit less off-targeting effects. Accordingly, in certain preferred embodiments, the subject MAP4K4-specific RNAi agents have low to moderate SCF. It should also be understood, however, that while low or moderate SCF is desirable, it is not essential for reduced off-targeting effects. As such, in certain embodiments, a sequence may fall within the range of high SCF (>6000) and still exhibits low off-targeting effects.

According to this aspect of the invention, certain sense or antisense modifications further increase nuclease stability, and/or lower interferon induction, without a significant decrease in RNAi activity (or no decrease in RNAi activity at all).

In certain embodiment of the invention, the dsRNA construct associates with an RNA-induced silencing complex (RISC).

In another embodiment, the dsRNA construct of the present invention is blunt-ended. In other embodiments, 5'- and/or 3'-end overhangs of 1-4 nucleotides may be present on one or both strands.

In further aspects, the present invention contemplates a composition comprising the dsRNA described herein and a pharmaceutically acceptable carrier or diluent.

Another aspect of the invention provides a method for inhibiting the expression of a MAP4K4 gene in a mammalian cell, comprising contacting the mammalian cell with any of the subject dsRNA constructs. Another aspect of the invention provides a method for inhibiting the expression of a MAP4K4 gene in a mammalian cell, comprising contacting the mammalian cell with a vector expressing at least one strand of any of the subject dsRNA constructs. The method may be carried out in vitro or in vivo, in, for example, mammalian cells in culture, such as a human cell in culture. The target cells (e.g., mammalian cell) may be contacted in the presence of a delivery reagent, such as a lipid (e.g., a cationic lipid), a liposome, beta-glucan, chitosan, polyethyleneimine (PEI), or any combination thereof.

Another aspect of the invention provides a method for inhibiting the expression of a target gene in a mammalian cell, comprising contacting the mammalian cell with a vector expressing at least one strand of the dsRNA according to the present methods.

It is contemplated that different features of the invention, such as the different sense and/or antisense strand modifications, may be combined except when indicated otherwise, in order to create RNAi constructs with multiple advantages or features over the conventional siRNA constructs. Furthermore, it is also contemplated that any of the modifications to the dsRNA as described in U.S. Provisional Application 61/065,335, filed on Feb. 11, 2008, entitled "MODIFIED RNAI POLYNUCLEOTIDES AND USES THEREOF", incorporated herein by reference in its entirety, may be applied to the present compositions and methods.

For example, for all applicable aspects of the invention, the antisense strand may comprise a 2'-modified ribose sugar, such as 2'-O-methyl modified nucleotide, at the $2^{nd}$ nucleotide on the 5'-end of the antisense strand and, preferably no other modified nucleotides. The dsRNA having such modification may have enhanced target specificity or reduced off-target silencing compared to a similar construct without the 2'-O-methyl modification at said position.

For all applicable aspects of the invention, the antisense strand may comprise at least four consecutive 2'-modified ribose sugars, such as 2'-O-methyl modified, 3'-end nucleotides with non-hydrolyzable internucleotide linkages, such as phosphothioate linkages.

For all applicable aspects of the invention, the 5'-end 12 nucleotides and the 3'-end 10 nucleotides of a 25-mer may be 2'-modified ribose sugars. The number of the modified bases may be adjusted depending on the overall length of the construct. For example, for a 27-mer, the 5'-end 12-14 nucleotides and the 3'-end 10-12 nucleotides may be 2'-modified nucleotides, etc.

For all applicable aspects of the invention, the dsRNA may comprise a mismatch nucleotide at the $2^{nd}$ nucleotide from the 3'-end of the sense strand.

Certain combinations of specific antisense and sense strand modifications may even result in unexpected advantages, as partly manifested by enhanced ability to inhibit target gene expression, enhanced serum stability, and/or increased target specificity, etc.

According to this embodiment of the invention, certain sense strand sequences may be cleaved by the RISC complex loaded with the Dicer-resistant guide sequence, at the position where an equivalent mRNA is cleaved. While not wishing to be bound by any particular theory, this is partly because the sense strand share the same or similar sequence as the target mRNA. Therefore, the subject dsRNA constructs include those with a sense strand that can be cleaved between the 10th and 11th 3'-end nucleotides.

In alternative embodiments, the constructs of the invention may have different lengths. In certain embodiments, the preferred lengths of the construct are 19-49 nucleotides in length. In certain embodiments, the length of the construct is greater than or equal to 22 nucleotides in length. In certain embodiments, the length of the construct is greater than or equal to 25 nucleotides in length. In certain embodiments, the length of the construct is 26, 27, 28, 29, 30, or 31-49 nucleotides in length. Other lengths are also possible, so long as the lower length limit is the minimal length for a Dicer substrate, and the upper limit is a length that generally will not trigger PKR response in a target cell. In certain embodiments, modifications may alter that upper limit such that longer lengths (such as 50, 60, 70, 80, 90, 100 bp) are tolerable.

In certain embodiments, the modified dsRNA may have improved stability in serum and/or cerebral spinal fluid compared to an unmodified dsRNA having the same sequence.

In certain embodiments, the dsRNA does not induce interferon response in primary cells, such as mammalian primary cells, including primary cells from human, mouse and other rodents, and other non-human mammals.

In certain embodiments, the dsRNA may also be used to inhibit expression of a target gene in an invertebrate organism.

To further increase the stability of the subject constructs in vivo, either end of the sense strand and/or the 3'-end of the antisense strand may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

In certain embodiments, alternating nucleotides on the ends of the sense and/or antisense strands comprise 2'-modified ribose sugars, and wherein each of the 2'-modified ribose sugars faces an unmodified nucleotide on the opposite strand. In certain embodiment, the first 2'-modified antisense nucleotide is the most 5'-end antisense nucleotide or the 2nd nucleotide from the 5'-end of the antisense strand.

In certain embodiments, the subject double-stranded RNA may be chemically cross-linked at one or more points, or linked by a nucleotide loop structure at one or both ends (e.g., a single-stranded hairpin structure or a circular structure). In one embodiment, the chemical cross-link or the loop of the hairpin structure is at the 3'-end of the antisense strand (e.g., linking the 3'-end of the antisense strand to the 5'-end of the sense strand). In another embodiment, the chemical cross-link or the loop of the hairpin structure is at the 5'-end of the antisense strand (e.g., linking the 3'-end of the sense strand to the 5'-end of the antisense strand. In these embodiments, other structural features of the cross-linked or looped constructs, such as 5'-end and 3'-end modifications on the sense strand and/or the other modifications on the antisense strand, are essentially the same as those for the dsRNA described herein.

Another aspect of the invention provides a method for improving the gene silencing effect of a small interference RNA (siRNA), comprising modifying the sense and/or antisense nucleotides of the siRNA to become any of the subject dsRNA constructs.

Single-Stranded Hairpin Structures

In another embodiment of the invention, the subject MAP4K4 sequences are incorporated in the context of a hairpin structure. It has been previously described that a hairpin structure formed from a single-stranded polynucleotide does not require processing, and indeed is not processed by Dicer or other Dicer-like Rnase III enzymes to participate in (RISC-mediated) RNA interference. See U.S. Provisional Application No. 61/135,855, filed Jul. 24, 2008, entitled "SHORT HAIRPIN RNAi CONSTRUCTS AND USES THEREOF" and U.S. Provisional Application filed on Oct. 30, 2008, entitled "mimRNA CONSTRUCTS AND USES THEREOF", incorporated herein by reference in their entire contents. The guide strand of such a hairpin structure becomes the single species of active RNAi reagent, and thus facilitates the development of RNAi reagents or therapeutics with higher target specificity, and better-defined biological activity and/or pharmacological property.

Another advantages of the mimRNA is the presence of single-stranded region (loop region). In some cases, single-stranded polynucleotides are a better substrates for cellular uptake. Furthermore, in some embodiments, the single-stranded (loop) region is chemically modified. For example, in some embodiments, the chemical modification may comprise phosphothioate. In some other embodiments, the chemical modification comprises 2'OME or 2' Fluoro or 2' deoxy. In yet other embodiments, the chemical modification is a combination of phosphorothioates with 2' OMe and 2' Fluoro. In other embodiments, the loop may be completely or partially replaced by a chemical linker that is flexible enough to allow folding back of the duplex polynucleotide.

Thus in another aspect, the invention provides a single-stranded polynucleotide mimRNA construct of 15-49 nucleotides in length, for inhibiting expression of a MAP4K4 gene, said polynucleotide comprising: (1) a 5'-stem sequence having a 5'-end, and (2) a 3'-stem sequence having a 3'-end, said 5'-stem sequence and 3'-stem sequence being sufficiently complementary to form a double-stranded stem, and (3) a single-stranded loop bridging the 5'-stem and 3'-stem sequences. The single-stranded loop may be 2-15 nucleotides in length, or preferably 4, 5, 6, 7, 8, 9, 10, or 11 nucleotides in length. The 5'-stem sequence (including any 5'-end overhangs) and at least a portion or all of said single-stranded loop form a guide strand/sequence that is complementary to a transcript of a target gene. Furthermore, the single-stranded polynucleotide mimRNA structure may be (1) resistant to cleavage by Dicer, (2) associates with RISC, and/or (c) inhibits its expression of the target gene in a guide sequence-dependent manner.

In another aspect, the invention provides a single-stranded polynucleotide mimRNA construct of 15-49 nucleotides in length, for inhibiting expression of a MAP4K4 gene, said polynucleotide comprising: (1) a 5'-stem sequence having a 5'-end, and (2) a 3'-stem sequence having a 3'-end, said 5'-stem sequence and 3'-stem sequence being sufficiently complementary to form a double-stranded stem, and (3) a single-stranded loop bridging the 5'-stem and 3'-stem sequences. The single-stranded loop may be 2-15 nucleotides in length, or preferably 4, 5, 6, 7, 8, 9, 10, 11, 12, 13, or 14 nucleotides in length, or more preferably 4, 5, 6, 7 nucleotides in length. In certain embodiments, the single-stranded loop is 4 or 6 nucleotides in length. In unmodified forms, the preferred length of the mimRNA stem region is around 10-13 bp. In certain embodiments, the double-stranded stem region is at least 11 bp in length, preferably at least 12 bp in length.

In certain embodiments, the guide sequence hybridizes to a target sequence on an mRNA of the MAP4K4 gene, wherein the target sequence is that is any one of SEQ ID NO. 1, 3, 5, 7, 9, 11, 12, 13, 15, 17, 19, 21, 23, 25, 27, 29, 31, 33, 35, 37, 39, 41, 43, 45, 47, 49, 50, 51, 53, 54, 55, 56 and 57.

While not wishing to be bound by any particular theory, it is believed that the duplex/stem length limitation may be partially defined by thermodynamic stability in cellular environments. Thus a group of chemical modifications known to enhance thermodynamic stability of a duplex region may be used to alter stem length. A non-limiting example of these chemical modifications might be LNA (locked nucleic acid) or MGB (minor groove binder). There are other chemical modifications with similar properties in the art. One or more stabilizing chemical modifications might be applied to the duplex region of short mimRNAs and convert otherwise non-functional entities to functional ones. Preferably, the modification is in a non-guide sequence region.

Since chemically modified mimRNA stem length can be as small as 6 base pairs, standard bioinformatics methods may be used to identify perfect or partially perfect inverted repeats (IR) regions and use them as additional MAP4K4 target sites for mimRNAs, further to the target MAP4K4 sequences identified in the present invention.

The 5'-stem sequence (including any 5'-end overhangs), the single-stranded loop, and at least a portion or all of the 31-stem sequence form a guide strand/sequence that is complementary to a transcript of a MAP4K4 gene. Furthermore, the single-stranded polynucleotide mimRNA structure may be (1) resistant to cleavage by Dicer, (2) associates with RISC, and/or (c) inhibits expression of the MAP4K4 gene in a guide sequence-dependent manner.

In certain embodiments, the polynucleotide does not contain any overhangs. In other embodiments, 5'- and/or 3'-end overhangs of 1-6 nucleotides (preferably 1, 2, or 3 nucleotide overhang) may be present on one or both ends of the polynucleotide. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the $2^{nd}$ nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the mimRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

According to this aspect of the invention, certain guide strand modifications further increase nuclease stability, and/or lower interferon induction, without significantly decreasing RNAi activity (or no decrease in RNAi activity at all).

For example, for all applicable aspects of the invention, the 5'-stem sequence may comprise a 2'-modified ribose sugar, such as 2'-O-methyl modified nucleotide, at the $2^{nd}$ nucleotide on the 5'-end of the polynucleotide and, preferably no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

The constructs of the invention may have different lengths. In certain embodiments, the preferred lengths of the mimRNA construct are 15-49 nucleotides in length. In certain embodiments, the length of the mimRNA construct is 25 or 26 nucleotides in length. Other lengths are also possible, so long as the double-stranded stem does not exceed a maximum length causing it to be a Dicer substrate. In certain preferred aspects, the maximum length of the double-stranded stem does not exceed 21 base pairs. In another aspect, the maximum length of the double-stranded stem does not exceed 19 base pairs. Additionally, the double-stranded stem may be shorter than 10 base pairs without negatively affecting the RNAi capability of the hairpin construct. In other embodiments, the length of the single-stranded loop may be varied to allow for enhanced stability, for example.

In certain embodiments, the guide strand comprises a 2'-O-methyl modified nucleotide at the $2^{nd}$ nucleotide on the 5'-end of the guide strand and no other modified nucleotides.

In certain embodiments, the modified hairpin structure may have improved stability in serum and/or cerebral spinal fluid compared to an unmodified hairpin structures having the same sequence.

In other embodiments, at least the first 10 nucleotides from the 5'-end of the polynucleotide are 100% complementary to the MAP4K4 gene transcript. More preferably, at least the first 12 nucleotides from the 5'-end of the polynucleotide are 100% complementary to the MAP4K4 gene transcript. In certain preferred embodiments, about the first 12 to 15 nucleotides from the 5'-end of the polynucleotide are 100% complementary to the MAP4K4 gene transcript.

In certain embodiments, only nucleotides 2 to 17 of the guide sequence/strand is complementary to the MAP4K4 sequence. The sequence complementarity may be partial, preferably, the guide sequence can hybridize to the MAP4K4 sequence under the physiological condition of the cell or under high stringency condition.

As described herein, a nucleic acid molecule is "hybridizable" to another nucleic acid molecule, such as a cDNA, genomic DNA, or RNA, when a single-stranded form of the nucleic acid molecule can anneal to the other nucleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. Low stringency hybridization conditions correspond to a $T_m$ (melting temperature) of 55° C., e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency conditions" are understood to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning, $2^{nd}$* ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$, for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" or "physiological conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

In certain embodiments, the hairpin structure does not induce interferon response in primary cells, such as mammalian primary cells, including primary cells from human, mouse and other rodents, and other non-human mammals. In certain embodiments, the hairpin structure may also be used to inhibit expression of a MAP4K4 gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The invention includes methods to inhibit expression of a MAP4K4 gene either in a cell in vitro, or in vivo. As such, the polynucleotide hairpin constructs of the invention are useful for treating a patient with a disease characterized by the overexpression of a MAP4K4 gene. In other embodiments, the polynucleotide hairpin constructs of the invention are useful for treating a condition that would benefit from inhibition of a MAP4K4 gene below physiological levels.

The MAP4K4 gene can be endogenous or exogenous (e.g., introduced into a cell by a virus or using recombinant DNA technology) to a cell. Such methods may include introduction of RNA into a cell in an amount sufficient to inhibit expression of the MAP4K4 gene, where the RNA is a hairpin structure. By way of example, such an RNA molecule may have a guide strand that is complementary to the nucleotide sequence of the MAP4K4 gene, such that the composition inhibits expression of the MAP4K4 gene. As described in the foregoing embodiments, the guide strand may be formed by the 5'-stem sequence (including any 5'-end overhangs) and all or a portion of the single-stranded loop region. Alternatively, the guide strand may be formed by the 5'-stem sequence (including any 5'-end overhangs), the entire loop region, and all or a portion of the 3'-stem sequence.

The invention also relates to vectors expressing the subject hairpin constructs, and cells comprising such vectors or the subject hairpin constructs. The cell may be a mammalian cell in vivo or in culture, such as a human cell.

The invention further relates to compositions comprising the subject hairpin constructs, and a pharmaceutically acceptable carrier or diluent.

Another aspect of the invention provides a method for inhibiting the expression of a target gene in a mammalian cell, comprising contacting the mammalian cell with any of the subject hairpin constructs.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a MAP4K4 gene in a mammalian cell, comprising contacting the mammalian cell with a vector expressing the subject hairpin constructs.

Generally, in certain aspects, the RNAi structures of the present invention mediate sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into to multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject RNAi constructs may mimic the dsRNA in the siRNA mechanism, or the microRNA in the miRNA mechanism.

As described herein, a MAP4K4 gene or protein includes the full-length version as well as any naturally occurring fragments thereof. Additionally, a MAP4K4 gene or protein includes any naturally occurring isoforms of MAP4K4.

More detailed aspects of the invention are described in the sections below.

II. Duplex Structure

Duplex Characteristics

Double-stranded oligonucleotides of the invention may be formed by two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Hairpin Characteristics

In a first embodiment, the hairpin structures of the present invention include a nucleic acid comprising a single-stranded RNA, such as a shRNA. The hairpin structure can include a double-stranded stem region formed from a 5'-stem sequence having a 5'-end ("5'-stem sequence") and a 3'-stem sequence having a 3'-end ("3'-stem sequence") that is complementary to the 5'-stem sequence. The hairpin structure can further include a single-stranded loop region. In a related embodiment, the single-stranded polynucleotide is a DNA strand comprising one or more modified deoxyribonucleotides. In yet another related embodiment, the single-stranded polynucleotide is an XNA strand, such as a peptide nucleic acid (PNA) strand or locked nucleic acid (LNA) strand. Further still, the single-stranded polynucleotide is a DNA/RNA hybrid.

Preferably the 5'-stem sequence and 3'-stem sequence are at least substantially complementary to each other, and more preferably about 100% complementary to each other. More preferably, the 5'-stem sequence and 3'-stem sequence are each 5 to 19 nucleotides, inclusive, in length. Alternatively, the 5'-stem sequence and 3'-stem sequence are each 10 to 19 nucleotides, inclusive, in length. Additionally, the 5'-stem sequence and 3'-stem sequence within any hairpin of the invention can be the same length, or differ in length by less than about 5 bases, which as persons skilled in the art are aware can appear in a hairpin structure as one or more bulge(s). Furthermore, preferably the loop structure is about 2 to 15 nucleotides in length, and more preferably 4-11 nucleotides.

Preferably, overhangs, if any, comprise between 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid. In the case of an overhang at the 5'-end of the polynucleotide, it is preferred that the modification(s) to the 5'-terminal nucleotide, if any, does not affect the RNAi capability of the hairpin construct. Such a modification can be, for example, a phosphorothioate.

As used herein, the term "double-stranded stem" includes one or more nucleic acid molecules comprising a region of the molecule in which at least a portion of the nucleomonomers are complementary and hydrogen bond to form a double-stranded region.

In other embodiments, the 3'-stem sequence comprises one or more universal base-pairing nucleotides.

In certain embodiments, a double-stranded stem of the hairpin construct contains mismatches and/or loops or bulges, but is double-stranded over at least about 50% of the length of the double-stranded stem. In another embodiment, a double-stranded stem of the invention is double-stranded over at least about 60% of the length of the stem. In another embodiment, a double-stranded stem of the hairpin construct is double-stranded over at least about 70% of the length of the stem. In another embodiment, a double-stranded stem of the hairpin is double-stranded over at least about 80% of the length of the stem. In another embodiment, a double-stranded stem of the hairpin construct is double-stranded over at least about 90%-95% of the length of the double-stranded stem. In another embodiment, a double-stranded stem of the hairpin construct is double-stranded over at least about 96%-98% of the length of the stem. In certain embodiments, the double-stranded stem of the hairpin construct contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a normaturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

In one embodiment, sense oligomers may have 2'-modifications on the ends (e.g., 2 on each end, 3 on each end, and 4 on each end, etc.; as well as 1 on one end, 2 on one end, 3 on one end, and 4 on one end, etc.; and even unbalanced combinations such as 12 on one end and 10 on the other end, etc.). Likewise, the antisense strand may have 2'-modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). In preferred aspects, the 2'-modifications are 2-O-methyl modifications in the sense RNA strand and/or the antisense strand.

According to the instant invention, the sense strand can tolerate many 2'-modifications (such as 2-O-methyl modifications), so long as the central linkages are unmodified. As used herein, "central" is not limited to mean the geometric mid-point of the sense strand. Rather, it can include any location between the 5'-end portion and the 3'-end portion of the sense strand. The 5'-end portion and the 3'-end portion of the sense strand need not be symmetrical.

Thus, in certain embodiments, the sense strand is not completely modified (i.e., at least one or more sense strand nucleotide(s) are unmodified). In certain embodiments, the unmodified sense strand nucleotides are in the central portion of the sense strand, or between the stretch of modified sense strand nucleotides on the 5'-end and the stretch of modified sense strand nucleotides on the 3'-end.

Also according to the instant invention, the sense strand tolerance for 2'-modification is not necessarily symmetrical. Rather, asymmetrical configurations may be desirable when using, for example, a sense strand of 25 or 26 nucleotides. 2'-mofications add nuclease stability, and reduce interferon induction, and are easier to synthesize. Thus it may be desirable to include more such 2'-modified ribose sugars (especially 2-O-methyl modified) on the sense strand, so long as the teachings of the instant invention is followed to preserve RNAi activity.

In some embodiments of the present invention, the subject highly modified sense strands may be combined with either unmodified or lightly modified antisense strands to allow maximum guide strand activity.

To further maximize endo- and exo-nuclease resistance, in addition to the use of 2'-modified nucleomonomers in the ends, inter-nucleomonomer linkages other than phosphodiesters may be used. For example, such end blocks may be used alone or in conjunction with phosphothioate linkages between the 2'-O-methly linkages. Preferred 2'-modified nucleomonomers are 2'-modified end nucleotides.

Although the antisense strand may be substantially identical to at least a portion of the target MAP4K4 gene (or genes), at least with respect to the base pairing properties, the sequence need not be perfectly identical to be useful. Generally, higher homology can be used to compensate for the use of a shorter antisense gene. In some cases, the antisense strand generally will be substantially identical (although in antisense orientation) to the MAP4K4 target gene.

One particular example of a composition of the invention has end-blocks on both ends of a sense oligonucleotide and only the 3'-end of an antisense oligonucleotide. Without wishing to be bound by theory, a 2-O-modified sense strand may work less well than its unmodified version, possibly because it is not efficiently unwound. Thus, in certain embodiments, mismatches may be introduced into specific positions of the sense strand (modified 2-O-methyl sense strand, or even unmodified sense strand) to facilitate easier loading into the RISC complex.

In some embodiments, the length of the sense strand can be 30, 29, 28, 27, 26, 25, 24, 23, 22, 21, 20, 19, or 18 nucleotides. Similarly, the length of the antisense strand can be 30, 29, 28, 27, 26, 25, 24, 23, 22, 21, 20, 19, or 18 nucleotides. Further, when a double-stranded nucleic acid molecule is formed from such sense and antisense molecules, the resulting duplex may have blunt ends or overhangs of 0, 1, 2, 3, 4, 5, 6, 7, 8, 9, 10, 11, 12, 13, or 14 nucleotides on one end or independently on each end. Further, double stranded nucleic acid molecules of the invention may be composed of a sense strand and an antisense strand wherein these strands are of lengths described above, and are of the same or different lengths, but share only 10, 11, 12, 13, 14, 15, 16, 17, 18, 19, or 20 nucleotides of sequence complementarity. By way of illustration, in a situation where the sense strand is 20 nucleotides in length and the antisense is 25 nucleotides in length and the two strands share only 15 nucleotides of sequence complementarity, a double stranded nucleic acid molecules may be formed with a 10 nucleotide overhang on one end and a 5 nucleotide overhang on the other end.

The use of 2'-O-methyl RNA may also be beneficially in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—$OCH_2CH{=}CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), to acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulffiydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —$O^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-30}(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2$—O—$(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—($PO^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-0 that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, the sense strand of an oligonucleotide comprises a 5' group that allows for RNAi activity but which renders the sense strand inactive in terms of gene targeting. Preferably, such a 5' modifying group is a phosphate group or a group larger than a phosphate group. Oligonucleotides of this type often exhibit increased specificity for a target gene in a cell that corresponds to the nucleotide sequence of the antisense strand. This is because the sense strand in such an oligonucleotide is often rendered incapable of mediating cleavage of any nucleotide sequence it might bind to non-specifically and thus will not inactivate any other genes in the cell. Thus, observed decrease in the expression of a MAP4K4 gene within a cell transfected with such an oligonucleotide will often be attributed to the direct or indirect effect of the antisense strand. Thus, according to another embodiment, the invention provides a method of increasing the specificity of an oligonucleotide for a target MAP4K4 gene in a cell, wherein said oligonucleotide comprises a sense strand and an antisense strand, wherein both the sense strand and the antisense strand are capable of binding to corresponding nucleotide sequences if present in said cell, said method comprising the step of modifying the 5' terminal hydroxy moiety of said sense strand with a phosphate group or a group larger than a phosphate group prior to contacting said oligonucleotide with said cell so as to render said sense strand incapable of mediating cleavage of any nucleotide sequence it might bind to non-specifically and thus will not inactivate any other genes in the cell.

Another way to increase target gene specificity, or to reduce off-target silencing effect, is to introduce a 2'-modification (such as the 2'-O methyl modification) at a position corresponding to the second 5'-end nucleotide of the Dicer-cleaved 21-mer. Applicants' discovery allows the positioning of this 2'-modification in the Dicer-resistant dsRNA, thus enabling one to design better siRNA constructs with less or no off-target silencing.

In one embodiment, a double-stranded oligonucleotide of the invention can comprise (i.e., be a duplex of) one nucleic acid molecule which is DNA and one nucleic acid molecule which is RNA. Antisense sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the sense strand nucleotides (2'-modified or not) are linked by phosphorothioate linkages. Such constructs tend to have improved pharmacokinetics due to their higher affinity for serum proteins. The phosphorothioate linkages in the sense strand generally do not interfere with guide strand activity, once the latter is loaded into RISC.

Antisense sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate intersubunit linkages. Morpholino oligonucleotides have many to advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

III. Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. No. 5,013,830; U.S. Pat. No. 5,214,135; U.S. Pat. No. 5,525,719; Kawasaki et al. 1993. *J. Med. Chem.* 36:831; WO 92/03568; U.S. Pat. No. 5,276,019; and U.S. Pat. No. 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC(SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

IV. Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet. 2003 Jan. 19:9; Reichhart J M et al. Genesis. 2002. 34(1-2):1604, Yu et al. 2002. Proc. Natl. Acad. Sci. USA 99:6047; Sui et al. 2002. Proc. Natl. Acad. Sci. USA 99:5515) viruses, polyamine or polycation conjugates using compounds such as polylysine, protamine, or Ni, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Conjugating Agents

Conjugating agents bind to the oligonucleotide in a covalent manner. In one embodiment, oligonucleotides can be derivatized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989*, FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974*, Biochem. Biophys. Acta* 340:323, and Lemaitre et al., 1987*, Proc. Natl. Acad. Sci. USA* 84:648).

Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides. Accordingly, the present invention provides for derivatization of oligonucleotides with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes, and steroids. A major advantage of using conjugating agents is to increase the initial membrane interaction that leads to a greater cellular accumulation of oligonucleotides.

Other conjugating agents include various vitamins, such as fat soluble vitamins, which may be used as a conjugate to deliver RNAi constructs specifically into adipose tissue—the primary location where these vitamins are stored. These vitamin-based conjugating agents may be especially useful for targeting certain metabolic disease targets, such as diabetes/obesity. Of the fat soluble vitamins, such as vitamins A, D, E, K, etc., vitamin K may be preferred in some embodiments, as there is no known upper intake level (although large doses could lead to breakdown of red blood cells and possibly to liver disease). In comparison, vitamins A and D have more defined toxicity and established upper intake levels.

In certain embodiments, gamma carboxyglutamic acid residues may be conjugated to the subject RNAi constructs to increased their membrane stickiness, and/or to slow clearance and improve general uptake (infra).

Certain conjugating agents that may be used with the instant constructs include those described in WO04048545A2 and US20040204377A1 (all incorporated herein by their entireties), such as a Tat peptide, a sequence substantially similar to the sequence of sequence ID number 12 of WO04048545A2 and US20040204377A1, a homeobox (hox) peptide, a MTS, VP22, MPG, at least one dendrimer (such as PAMAM), etc.

Other conjugating agents that may be used with the instant constructs include those described in WO07089607A2 (incorporated herein), which describes various nanotransporters and delivery complexes for use in delivery of nucleic acid molecules (such as the subject dsRNA constructs) and/or other pharmaceutical agents in vivo and in vitro. Using such delivery complexes, the subject dsRNA can be delivered while conjugated or associated with a nanotransporter comprising a core conjugated with at least one functional surface group. The core may be a nanoparticle, such as a dendrimer (e.g., a polylysine dendrimer). The core may also be a nanotube, such as a single walled nanotube or a multi-walled nanotube. The functional surface group is at least one of a lipid, a cell type specific targeting moiety, a fluorescent molecule, and a charge controlling molecule. For example, the targeting moiety may be a tissue-selective peptide. The lipid may be an oleoyl lipid or derivative thereof. Exemplary nanotransporter include NOP-7 or HBOLD.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Methods and compositions for delivering nucleic acid molecules are also incorporated by reference from U.S. Provisional Applications 61/192,954, filed on Sep. 22, 2008, 61/149,946, filed on Feb. 4, 2009 and 61/224,031, filed on Jul. 8, 2009.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane) carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. No. 4,235,871; U.S. Pat. Nos. 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated I fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the (3 turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. *J. Cell Biol.* 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies or protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

V. Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended to immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified to oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 μm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and antioxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regime may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

VI. Therapeutic Use

By inhibiting the expression of a MAP4K4 gene, the oligonucleotide compositions of the present invention can be used to treat any disease involving the expression of a MAP4K4 protein. The inhibition of a MAP4K4 gene includes any fragments and isoforms of MAP4K4. Diseases that can be treated by oligonucleotide compositions in accordance with the present methods include, just to illustrate: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), and cardiovascular diseases.

Some specific examples of conditions that may benefit from the inhibition of MAP4K4 include, for example, metabolic disorders. Metabolic disorders, or metabolic syndrome, is described by accepted synonyms, which includes, but is not limited to, syndrome X, insulin resistance syndrome, insulin-resistant hypertension, the metabolic hypertensive syndrome, dysmetabolic syndrome. Components of the metabolic syndrome include, but is not limited to, glucose intolerance, impaired glucose tolerance, impaired fasting serum glucose, impaired fasting blood glucose, hyperinsulinemia, pre-diabetes, obesity, visceral obesity, hypertriglyceridemia, elevated serum concentrations of free fatty acids, elevated serum concentrations of C-reactive protein, elevated serum concentrations of lipoprotein(a), elevated serum concentrations of homocysteine, elevated serum concentrations of small, dense low-density lipoprotein (LDL)-cholesterol, elevated serum concentrations of lipoprotein-associated phospholipase (A2), reduced serum concentrations of high density lipoprotein (HDL)-cholesterol, reduced serum concentrations of HDL (2b)-cholesterol, reduced serum concentrations of adiponectin, adipogenesis, and albuminuria.

In addition, MAP4K4 silencing has been implicated in the inhibition of the migration of multiple carcinoma cell lines (Collins et al., 2006, *Proc. Natl. Acad. Sci.* 103(10):3775-3780). Accordingly, it is contemplated that the use of MAP4K4 RNAi constructs according to the present invention may benefit certain types of cancers in which inhibition of tumor cell motility is desired.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08,003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Molecular Cloning A Laboratory Manual,* 2nd Ed., ed. by Sambrook, J. et al. (Cold Spring Harbor Laboratory Press (1989)); *Short Protocols in Molecular Biology,* 3rd Ed., ed. by Ausubel, F. et al. (Wiley, N.Y. (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J.

Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, *J. Experiments in Molecular Genetics* (Cold Spring Harbor Press, Cold Spring Harbor, N.Y. (1972)).

EXAMPLES

The invention now being generally described, it will be more readily understood by reference to the following examples, which are included merely for purposes of illustration of certain aspects and embodiments of the present invention, and are not intended to limit the invention. Although the examples below demonstrate silencing of MAP4K4 using a select number of siRNA duplexes having particular chemistry, it is understood that any of the RNA chemistry described herein may be applied for the present methods.

Example 1

RNA Screen to Identify Lead Sequences within MAP4K4

HEK293 cells were transfected at 0.1 nM active RNA concentration. Target mRNA was measured 24 hours post-transfection using the methods described below. Three duplex sequences (10, 20 and 21) were chosen as lead hits based on their activity, seed complement frequency (SCF), and homology to the mouse MAP4K4 gene, as described below.

All duplexes used in the examples described herein are modified on the sense strand, but not on the antisense (guide) strand. The sense strands have been modified to include 2'OMe on 12 of the 5'-most end nucleotides and on 10 of the 3'-most nucleotides. The antisense strand complements the sense strand to form a blunt-ended duplex of 25 base-pairs.

Transfections were performed in HEK293 cells using LIPOFECTAMINE™ RNAiMax (Invitrogen) following the manufacture's procedures. In all studies, duplex candidates were co-transfected with non-targeting Luciferase control siRNA (Invitrogen) to a constant total concentration of 25 nM to allow for efficient complexing of the siRNAs and LIPOFECTAMINE™ RNAiMAX. Target mRNA levels were measured using a bDNA assay (Panomics QUANTIGENE®) 24 hours post-transfection. In this assay, MAP4K4 mRNA was normalized to Cyclophilin B (PPIB) mRNA.

The bDNA assay is a sandwich nucleic acid hybridization method that uses bDNA molecules to amplify signal from captured target RNA. According to the manufacturer, bDNA technology forms the basis of the FDA-approved clinical diagnostic VERSANT 3.0 assays for HIV, HCV and HBV viral load, that are offered commercially by Siemens and have been in use for over a decade. Another advantage of bDNA assays is that RNA is measured directly from the sample source, without RNA purification or enzymatic manipulation, thereby avoiding inefficiencies and variability introduced by or errors inherent to these processes.

The results were plotted and are shown in FIG. 1, which depicts the entire length of the MAP4K4 gene. Each bar represents the silencing efficacy of a particular 25 base pair siRNA duplex which targets a region on MAP4K4 starting at the indicated start site. It can be seen, for example, that duplex sequences spanning the positions 2334 to 2345 of MAP4K4 are effective silencers. Generally, duplexes which effectively reduced target mRNA expression by more than 60% at a 0.1 nM dose were selected, which are listed in Table 1. However, sequences having low to moderate SCF are preferred, though not necessary, for the purpose of reducing potential off-targeting effects, as confirmed bioinformatically by Anderson et al. Additionally, to allow ease of pre-clinical testing in mice, sequences that lie in regions that share high sequence homology between human and mouse sequences (e.g, those that are at least 95% homologous to the corresponding mouse sequence) are preferable.

TABLE 1

Sequences that effectively reduced target mRNA expression by more than 60% at 0.1 nM in initial screen.

| Start Site | Sense Sequence (5'-3') | AntiSense Sequence (5'-3') | <40% expression remaining at 0.1 nM | Seed region freq. | Duplex number |
|---|---|---|---|---|---|
| 522 | GCCAGAAUGUGUUGCUGACUGAGAA (SEQ ID NO: 1) | UUCUCAGUCAGCAACACAUUCUGGC (SEQ ID NO: 2) | Yes (33.08%) | 7073 | 1 |
| 541 | UGAGAAUGCAGAGGUGAAACUUGUU (SEQ ID NO: 3) | AACAAGUUUCACCUCUGCAUUCUCA (SEQ ID NO: 4) | Yes (39.39%) | 5876 | 2 |
| 764 | CAUCCAAUGAGAGCACUGUUUCUCA (SEQ ID NO: 5) | UGAGAAACAGUGCUCUCAUUGGAUG (SEQ ID NO: 6) | Yes (38.32%) | 8788 | 3 |
| 926 | GAUCAGCCAAAUGAAAGGCAAGUUA (SEQ ID NO: 7) | UAACUUGCCUUUCAUUUGGCUGAUC (SEQ ID NO: 8) | Yes (24.47%) | 5032 | 4 |
| 928 | UCAGCCAAAUGAAAGGCAAGUUAGA (SEQ ID NO: 9) | UCUAACUUGCCUUUCAUUUGGCUGA (SEQ ID NO: 10) | Yes (17.53%) | 3328 | 5 |
| 938 | GAAAGGCAAGUUAGAAUCCAGCUUA (SEQ ID NO: 13) | UAAGCUGGAUUCUAACUUGCCUUUC (SEQ ID NO: 14) | Yes (37.16%) | 6800 | 6 |
| 1271 | AGGCGACGGCUAGAAGAGCAACAAA (SEQ ID NO: 15) | UUUGUUGCUCUUCUAGCCGUCGCCU (SEQ ID NO: 16) | Yes (31.09%) | 4481 | 7 |
| 2071 | AGAUGUACGGCCACCUCACAAAGUA (SEQ ID NO: 17) | UACUUUGUGAGGUGGCCGUACAUCU (SEQ ID NO: 18) | Yes (39.47%) | 6216 | 8 |

TABLE 1-continued

Sequences that effectively reduced target mRNA expression by more than 60% at 0.1 nM in initial screen.

| Start Site | Sense Sequence (5'-3') | AntiSense Sequence (5'-3') | <40% expression remaining at 0.1 nM | Seed region freq. | Duplex number |
|---|---|---|---|---|---|
| 2334 | AGUCCGCUAGUAGCACACUCCAGAA (SEQ ID NO: 19) | UUCUGGAGUGUGCUACUAGCGGACU (SEQ ID NO: 20) | Yes (37.24%) | 6617 | 9 |
| 2337 | CCGCUAGUAGCACACUCCAGAAACA (SEQ ID NO: 21) | UGUUUCUGGAGUGUGCUACUAGCGG (SEQ ID NO: 22) | Yes (31.97%) | 7018 | 10 |
| 2339 | GCUAGUAGCACACUCCAGAAACACA (SEQ ID NO: 23) | UGUGUUUCUGGAGUGUGCUACUAGC (SEQ ID NO: 24) | Yes (38.73%) | 6029 | 11 |
| 2345 | AGCACACUCCAGAAACACAAAUCUU (SEQ ID NO: 25) | AAGAUUUGUGUUUCUGGAGUGUGCU (SEQ ID NO: 26) | Yes (36.87%) | 5074 | 12 |
| 2574 | ACAAGAAGAGGUUUAACUCUGAGAU (SEQ ID NO: 27) | AUCUCAGAGUUAAACCUCUUCUUGU (SEQ ID NO: 28) | Yes (39.00%) | 7073 | 13 |
| 2577 | AGAAGAGGUUUAACUCUGAGAUUCU (SEQ ID NO: 29) | AGAAUCUCAGAGUUAAACCUCUUCU (SEQ ID NO: 30) | Yes (33.55%) | 4427 | 14 |
| 2681 | AAGGUCUAUCCUCUUAUCAACCGAA (SEQ ID NO: 31) | UUCGGUUGAUAAGAGGAUAGACCUU (SEQ ID NO: 32) | Yes (27.61%) | 886 | 15 |
| 2692 | UCUUAUCAACCGAAGACGAUUUCAA (SEQ ID NO: 33) | UUGAAAUCGUCUUCGGUUGAUAAGA (SEQ ID NO: 34) | Yes (38.00%) | 7989 | 16 |
| 2743 | UGUCUUGGUGACAAUAUCUGGCAAA (SEQ ID NO: 35) | UUUGCCAGAUAUUGUCACCAAGACA (SEQ ID NO: 36) | Yes (38.08%) | 5188 | 17 |
| 2778 | UACGUGUCUACUAUUUGUCCUGGUU (SEQ ID NO: 37) | AACCAGGACAAAUAGUAGACACGUA (SEQ ID NO: 38) | Yes (35.54%) | 1710 | 18 |
| 2780 | CGUGUCUACUAUUUGUCCUGGUUAA (SEQ ID NO: 39) | UUAACCAGGACAAAUAGUAGACACG (SEQ ID NO: 40) | Yes (21.65%) | 4185 | 19 |
| 2926 | GAUUGCUUUGAAGAGUUCUGUGGAA (SEQ ID NO: 41) | UUCCACAGAACUCUUCAAAGCAAUC (SEQ ID NO: 42) | Yes (28.04%) | 6915 | 20 |
| 3028 | ACUGGUGGAUCUCACUGUUGAGGAA (SEQ ID NO: 43) | UUCCUCAACAGUGAGAUCCACCAGU (SEQ ID NO: 44) | Yes (29.25%) | 6543 | 21 |
| 3103 | UGAUGUGGAUUCAGGAUCAGUCUAU (SEQ ID NO: 45) | AUAGACUGAUCCUGAAUCCACAUCA (SEQ ID NO: 46) | Yes (31.46%) | 4583 | 22 |
| 3110 | GAUUCAGGAUCAGUCUAUGACAUUU (SEQ ID NO: 47) | AAAUGUCAUAGACUGAUCCUGAAUC (SEQ ID NO: 48) | Yes (35.50%) | 6325 | 23 |

Example 2

$EC_{50}$ Analysis of siRNA Duplexes Based Off of Lead Sequences (Duplexes 10, 20 and 21)

$EC_{50}$ analyses were performed with duplexes whose sequences are based off of select duplexes from Example 1 (i.e., 10, 20 and 21). In the RNA screen above, duplexes which effectively reduced target mRNA expression by more than 60% at a 0.1 nM dose were used to design and test additional duplexes. Additional selection factors are described in Example 1. The additional sequences derived from the initial selected sequences are shown in Table 2, and the efficacy of each duplex is presented below. Table 2 compares each human sequence to the corresponding mouse sequence; mismatches, if any, are underlined and bolded in the mouse sequence.

Figure 2A:
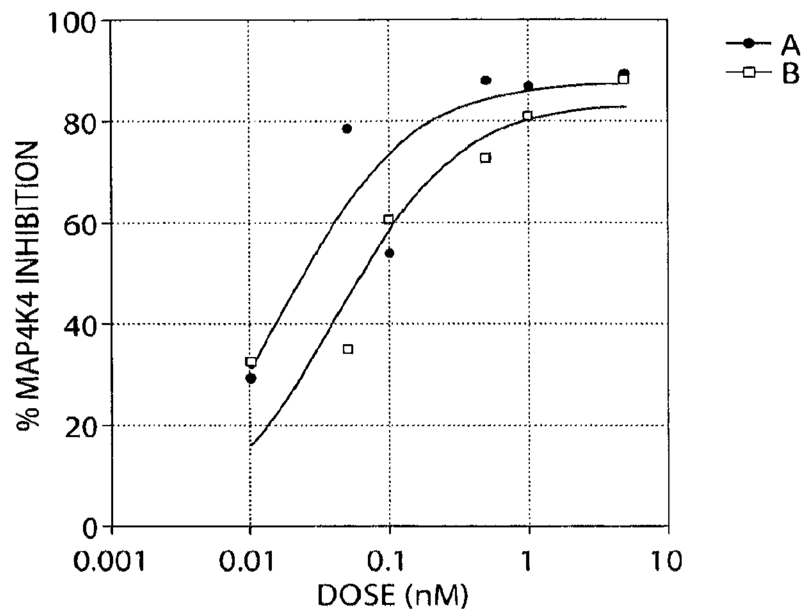
FIG. 2A shows an $EC_{50}$ analysis of MAP4K4 siRNA duplexes containing sense strands corresponding to SEQ ID NOs:43 or 50 based off of sequences surrounding the duplex 21 site identified in the RNA screen. MAP4K4 expression was measured using a bDNA hybridization assay (Panomics) 48 hours post-transfection. On the graph, "A" corresponds to an RNA duplex containing a sense strand corresponding to SEQ ID NO:43, and "B" corresponds to an RNA duplex containing a sense strand corresponding to SEQ ID NO:50.

FIG. 2A shows the results of duplexes that are based off of the duplex sequence 21, namely, sequences containing sense strands corresponding to SEQ ID NOs:43 or 50 (see Table 2 below). MAP4K4 expression was measured using cDNA hybridization assay as described above at 48 hours post-transfection. The $EC_{50}$ values of these duplexes are as follows:

Duplex containing SEQ ID NO:43: 0.042 nM±0.017 nM

Duplex containing SEQ ID NO:50: 0.018 nM±0.009 nM

Figure 2B:
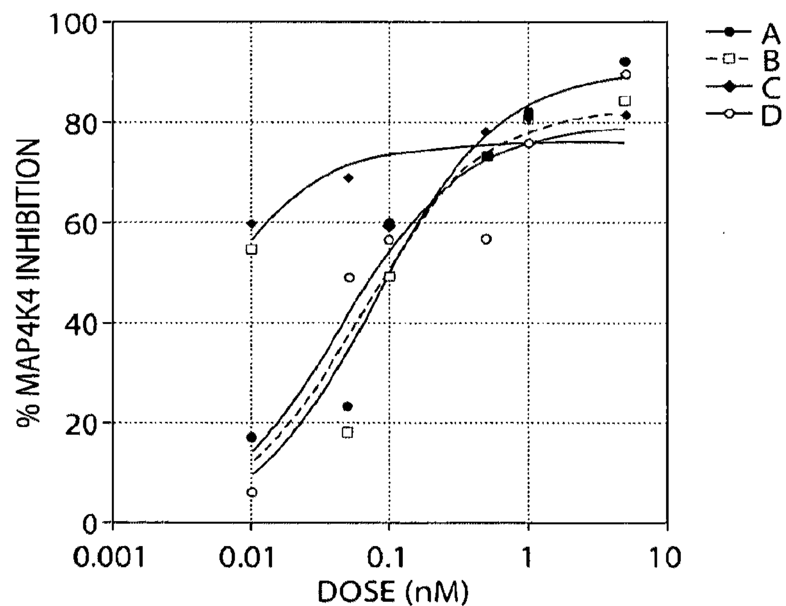
FIG. 2B shows an $EC_{50}$ analysis of MAP4K4 siRNA duplexes containing sense strands corresponding to SEQ ID NOs:41, 56, 11 or 12 based off of sequences surrounding the duplex 20 site identified in the RNA screen. MAP4K4 expression was measured using a bDNA hybridization assay (Panomics) 48 hours post-transfection. On the graph, "A" corresponds to an RNA duplex containing a sense strand corresponding to SEQ ID NO:41, "B" corresponds to an RNA duplex containing a sense strand corresponding to SEQ ID NO:56, "C" corresponds to an RNA duplex containing a sense strand corresponding to SEQ ID NO:11, and "D" corresponds to an RNA duplex containing a sense strand corresponding to SEQ ID NO:12.

FIG. 2B shows the results of duplexes that are based off of the duplex sequence 20, namely, sequences containing sense strands corresponding to SEQ ID NOs:11, 12, 41 or 56 (see Table 2 below). MAP4K4 expression was measured using cDNA hybridization assay as described above at 48 hours post-transfection. The $EC_{50}$ values of these duplexes are as follows:

Duplex containing SEQ ID NO:41: 0.081 nM±0.027 nM

Duplex containing SEQ ID NO:56: 0.062 nM±0.059 nM

Duplex containing SEQ ID NO:11: 0.003 nM±0.002 nM

Duplex containing SEQ ID NO:12: 0.046 nM±0.022 nM

Figure 2C:
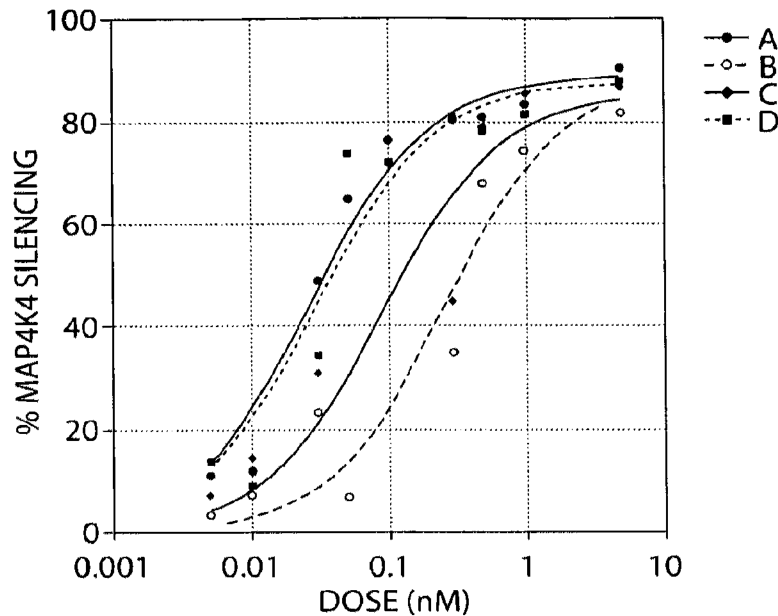
FIG. 2C shows an $EC_{50}$ analysis of MAP4K4 siRNA duplexes containing sense strands corresponding to SEQ ID NOs:21, 53, 19 or 54 based off of sequences surrounding the duplex 10 site identified in the RNA screen. MAP4K4 expression was measured using a bDNA hybridization assay (Panomics) 48 hours post-transfection. On the graph, "A" corresponds to an RNA duplex containing a sense strand corresponding to SEQ ID NO:21, "B" corresponds to an RNA duplex containing a sense strand corresponding to SEQ ID NO:53, "C" corresponds to an RNA duplex containing a sense strand corresponding to SEQ ID NO:19, and "D" corresponds to an RNA duplex containing a sense strand corresponding to SEQ ID NO:54.

FIG. 2C shows the results of duplexes that are based off of the duplex sequence 10, namely, sequences containing sense strands corresponding to SEQ ID NOs:21, 53, 19 or 54 (see Table 2 below). MAP4K4 expression was measured using cDNA hybridization assay as described above at 48 hours post-transfection. The $EC_{50}$ values of these duplexes are as follows:

Duplex containing SEQ ID NO:21: 0.030 nM±0.009 nM

Duplex containing SEQ ID NO:53: 0.266 nM±0.110 nM

Duplex containing SEQ ID NO:19: 0.091 nM±0.054 nM

Duplex containing SEQ ID NO:54: 0.027 nM±0.005 nM

Example 3

$EC_{50}$ Comparison of Lead siRNA Duplexes Selected for Future Studies

Figure 3:
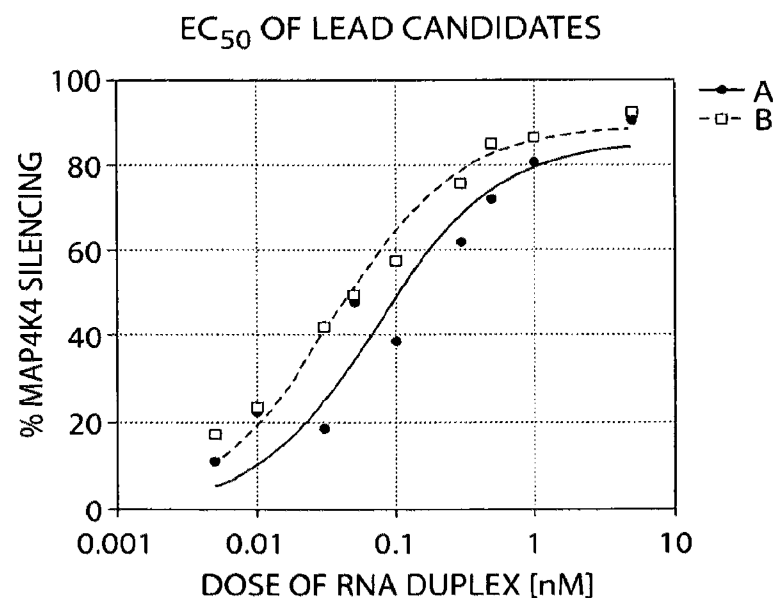
FIG. 3 shows an $EC_{50}$ analysis of two lead MAP4K4 duplexes: 24 and 25. MAP4K4 expression was measured using a bDNA hybridization assay (Panomics) 48 hours post-transfection.

Two lead duplexes, 24 and 25, were selected for future studies in mice. A side-by-side comparison of their $EC_{50}$ is shown in FIG. 3. The assay conditions for this analysis are similar to those described in Examples 1 and 2. The $EC_{50}$ values of these duplexes are as follows:

Duplex 24: 0.073 nM±0.023 nM

Duplex 25: 0.037 nM±0.005 nM

The average $EC_{50}$ values for all duplexes evaluated in Examples 2 and 3 are shown in Table 2.

TABLE 2

Additional sequences derived from duplex sequences 10, 20, or 21 selected based on initial RNA screen. "Start Site (H)" and "Start Site (M)" indicate the starting position of each sequence in the human or mouse MAP4K4, respectively.

| Start Site (H) | Human Sense Sequence (5'-3') | Start Site (M) | Homology to Mouse | Seed region freq. | AVG $EC_{50}$ Value (nM) |
|---|---|---|---|---|---|
| 3028 | ACUGGUGGAUCUCACUGUUGAGGAA (SEQ ID NO: 43) human<br>ACUGGUGGAUCUCACUGUGGAGGAA (SEQ ID NO: 49) mouse | 3518 | 96% (1 MM in seed) | 6543 | 0.043 |
| 3032 | CAUUACUGGUGGAUCUCACUGUUGA (SEQ ID NO: 50) human<br>CAUUACUGGUGGAUCUCACUGUGGA (SEQ ID NO: 51) mouse | 3514 | 96% (1 MM in seed) | 6602 | 0.032 |
| 2337 | CCGCUAGUAGCACACUCCAGAAACA (SEQ ID NO: 21) human<br>CCGCUAGUAGCACACUCCAGAAACA (SEQ ID NO: 21) mouse | 2827 | 100% | 7018 | 0.099 |
| 2335 | GUCCGCUAGUAGCACACUCCAGAAA (SEQ ID NO: 53) human<br>GUCCGCUAGUAGCACACUCCAGAAA (SEQ ID NO: 53) mouse | 2825 | 100% | 7069 | 0.144 |
| 2334 | AGUCCGCUAGUAGCACACUCCAGAA (SEQ ID NO: 19) human<br>AGUCCGCUAGUAGCACACUCCAGAA (SEQ ID NO: 19) mouse | 2824 | 100% | 6617 | 0.067 |
| 2333 | CAGUCCGCUAGUAGCACACUCCAGA (SEQ ID NO: 54) human<br>CAGUCCGCUAGUAGCACACUCCAGA (SEQ ID NO: 54) mouse | 2823 | 100% | 8216 | 0.281 |
| 2926 | GAUUGCUUUGAAGAGUUCUGUGGAA (SEQ ID NO: 41) human<br>AAUUGCUUUGAAGAGUUCUGUGGAA (SEQ ID NO: 55) mouse | 3416 | 96% (1 MM in non-seed) | 6915 | 0.054 |
| 2925 | UGAUUGCUUUGAAGAGUUCUGUGGA (SEQ ID NO: 56) human<br>UAAUUGCUUUGAAGAGUUCUGUGGA (SEQ ID NO: 57) mouse | 3415 | 96% (1 MM in non-seed) | 8125 | 0.146 |
| 2931 | CUUUGAAGAGUUCUGUGGAAGUCUA (SEQ ID NO: 11) human<br>CUUUGAAGAGUUCUGUGGAAGUCUA (SEQ ID NO: 11) mouse | 3421 | 100% | 5328 | 0.027 |
| 2932 | UUUGAAGAGUUCUGUGGAAGUCUAU (SEQ ID NO: 12) human<br>UUUGAAGAGUUCUGUGGAAGUCUAU (SEQ ID NO: 12) mouse | 3422 | 100% | 3136 | 0.175 |

TABLE 3

Sequences of lead duplexes that were selected based on activity, mouse homology, and other beneficial attributes for development. The two duplexes were moved into mouse studies.

| Sense Sequence (5'-3') | AntiSense Sequence (5'-3') | Duplex # |
|---|---|---|
| AGUCCGCUAGUAGCA CACUCCAGAA (SEQ ID NO: 19) | UUCUGGAGUGUGCUACUA GCGGACU (SEQ ID NO: 20) | 24 |

TABLE 3-continued

Sequences of lead duplexes that were selected based on activity, mouse homology, and other beneficial attributes for development. The two duplexes were moved into mouse studies.

| Sense Sequence (5'-3') | AntiSense Sequence (5'-3') | Duplex # |
|---|---|---|
| CUUUGAAGAGUUCUG UGGAAGUCUA (SEQ ID NO: 11) | UAGACUUCCACAGAACUC UUCAAAG (SEQ ID NO: 52) | 25 |

The invention claimed is:

1. A blunt-ended double-stranded RNA (dsRNA) for inhibiting expression of a MAP4K4 gene, comprising:

(1) a sense strand of 25, 26, 27, 28, 29 or 30 nucleotides in length, having a 5'-end and a 3'-end, wherein the sense strand is highly modified with 2'-modified ribose sugars, comprising a continuous stretch of 2'-modified ribose sugars on the 5'-end, a continuous stretch of 2'-modified ribose sugars on the 3'-end and a central region that is unmodified, and, (2) an antisense strand of 25, 26, 27, 28, 29 or 30 nucleotides in length, having a 5'-end and a 3'-end, which hybridizes to the sense strand, wherein the sense strand comprises a sequence selected from the group consisting of: SEQ ID NO: 1, 3, 5, 7, 11, 12, 13, 15, 17, 19, 21, 25, 27, 31, 33, 35, 37, 45 and 50, and wherein the dsRNA does not form a hairpin.

2. The dsRNA of claim 1, wherein the dsRNA comprises a modification of a base, and/or a phosphodiester linkage.

3. The dsRNA of claim 1, wherein the dsRNA comprises a hydrophobic modification of one or more bases.

4. The dsRNA of claim 1, wherein the dsRNA is 25-27 base pairs in length, and wherein the sense strand of the dsRNA comprises 12-14 and 10-12 consecutive 2'-modified ribose sugars at the 5'-end of the sense strand and the 3'-end of the sense strand, respectively.

5. A composition comprising the dsRNA of claim 1, and a pharmaceutically acceptable carrier or diluent.

6. A method for inhibiting the expression of a MAP4K4 gene in a mammalian cell, comprising contacting the mammalian cell with the dsRNA of claim 1.

7. A method of treating a patient for a disease characterized by overexpression of a MAP4K4 gene, comprising administering to the patient the dsRNA of claim 1, wherein the dsRNA mediates reduction in MAP4K4 expression.

8. The dsRNA of claim 1, wherein the sense strand comprises SEQ ID NO:11.

9. The dsRNA of claim 1, wherein the sense strand comprises SEQ ID NO:19.

10. The dsRNA of claim 1, wherein the sense strand comprises SEQ ID NO:50.

11. The dsRNA of claim 1, wherein the antisense strand comprises a sequence selected from the group consisting of SEQ ID NO. 2, 4, 6, 8, 10, 14, 16, 18, 20, 22, 24, 26, 28, 30, 32, 34, 36, 38, 40, 42, 44, 46, 48 and 52.

* * * * *